(12) United States Patent
Li et al.

(10) Patent No.: US 6,608,237 B1
(45) Date of Patent: Aug. 19, 2003

(54) HIGH-STRENGTH, STABILIZED ABSORBENT ARTICLE

(75) Inventors: Yong Li, Appleton, WI (US); Wendy Lynn Van Dyke, Appleton, WI (US); Gary Douglas Williams, Neenah, WI (US); Anthony John Wisneski, Kimberly, WI (US); Bernhardt Edward Kressner, Appleton, WI (US); Sridhar Ranganathan, Suwanee, GA (US); Michael Franklin Kalmon, Atoka, TN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 230 days.

(21) Appl. No.: 09/631,494

(22) Filed: Aug. 3, 2000

(51) Int. Cl.[7] ................................................ A61F 13/14
(52) U.S. Cl. ...................................... 604/382; 604/364
(58) Field of Search ............................... 604/364, 375, 604/382, 385.01, 385.23, 385.31

(56) References Cited

U.S. PATENT DOCUMENTS

| | | |
|---|---|---|
| 2,757,150 A | 7/1956 | Heritage |
| 3,082,138 A | 3/1963 | Hjelt |
| 3,453,355 A | 7/1969 | Rudloff |
| 3,658,613 A | 4/1972 | Steiger |
| 3,819,470 A | 6/1974 | Shaw et al. |
| 3,901,236 A | 8/1975 | Assarsson et al. |
| 3,903,889 A | 9/1975 | Torr |
| 4,076,663 A | 2/1978 | Masuda et al. |
| 4,286,082 A | 8/1981 | Tsubakimoto et al. |
| 4,410,571 A | 10/1983 | Korpman |
| 4,412,036 A | 10/1983 | Pedersen et al. |
| 4,467,012 A | 8/1984 | Pedersen et al. |
| 4,495,119 A | 1/1985 | Chung |
| 4,543,410 A | 9/1985 | Cruz, Jr. |
| 4,551,377 A | 11/1985 | Elves et al. |
| 4,573,989 A | 3/1986 | Karami et al. |
| 4,584,357 A | 4/1986 | Harding |
| 4,600,462 A | 7/1986 | Watt |
| 4,663,220 A | 5/1987 | Wisneski et al. |
| 4,666,647 A | 5/1987 | Enloe et al. |
| 4,676,196 A | 6/1987 | Lojek et al. |
| 4,699,823 A | 10/1987 | Kellenberger et al. |
| 4,704,116 A | 11/1987 | Enloe |
| 4,753,646 A | 6/1988 | Enloe |
| 4,761,258 A | 8/1988 | Enloe |
| 4,822,453 A | 4/1989 | Dean et al. |
| 4,853,086 A | 8/1989 | Graef |

(List continued on next page.)

FOREIGN PATENT DOCUMENTS

| | | |
|---|---|---|
| GB | 1251753 | 10/1971 |
| GB | 1356100 | 6/1974 |
| GB | 2015604 A | 9/1979 |
| WO | WO 92/07985 A1 | 5/1992 |
| WO | WO 96/06223 A1 | 2/1996 |
| WO | WO 98/20821 A1 | 5/1998 |

*Primary Examiner*—Weilun Lo
*Assistant Examiner*—Michael Bogart
(74) *Attorney, Agent, or Firm*—Paul Yee; Thomas M. Parker

(57) ABSTRACT

An absorbent article (10) includes a backsheet layer (30), a liquid permeable topsheet layer (28), and an absorbent body (32) sandwiched between the backsheet and topsheet layers. The absorbent body (32) includes a first fibrous stratum (52) having a first quantity of absorbent fibers, a second fibrous stratum (54) having a second quantity of absorbent fibers, and at least a third fibrous stratum (56) which is located between and integrally formed with the first and second fibrous strata (52, 54). In particular aspects, the third fibrous stratum (56) includes an operative quantity of a substantially hydrophilic, wet-strength agent. In other aspects, the wet-strength agent is distributed in the third quantity of absorbent fibers to render the third fibrous stratum (56) substantially non-dispersible.

27 Claims, 18 Drawing Sheets

U.S. PATENT DOCUMENTS

| | | |
|---|---|---|
| 4,889,595 A | 12/1989 | Herron et al. |
| 4,927,582 A | 5/1990 | Bryson |
| 4,935,022 A | 6/1990 | Lash et al. |
| 4,938,753 A | 7/1990 | Van Gompel et al. |
| 4,977,892 A * | 12/1990 | Ewall .......................... 128/156 |
| 5,013,309 A | 5/1991 | Baigas, Jr. et al. |
| 5,015,245 A | 5/1991 | Noda |
| 5,028,224 A | 7/1991 | Pieper et al. |
| 5,064,689 A | 11/1991 | Young, Sr. et al. |
| 5,071,681 A | 12/1991 | Manning et al. |
| 5,171,237 A | 12/1992 | Poccia et al. |
| 5,188,624 A | 2/1993 | Young, Sr. et al. |
| 5,226,992 A | 7/1993 | Morman |
| 5,227,107 A | 7/1993 | Dickenson et al. |
| 5,230,959 A | 7/1993 | Young, Sr. et al. |
| 5,246,429 A | 9/1993 | Poccia et al. |
| 5,262,218 A | 11/1993 | Putzier |
| 5,300,192 A | 4/1994 | Hansen et al. |
| 5,308,896 A | 5/1994 | Hansen et al. |
| 5,350,370 A | 9/1994 | Jackson et al. |
| 5,352,480 A | 10/1994 | Hansen et al. |
| 5,360,420 A | 11/1994 | Cook et al. |
| 5,378,528 A | 1/1995 | Makoui |
| 5,399,219 A | 3/1995 | Roessler et al. |
| 5,405,501 A | 4/1995 | Phan et al. |
| 5,429,788 A | 7/1995 | Ribble et al. |
| 5,432,000 A | 7/1995 | Young, Sr. et al. |
| 5,445,777 A | 8/1995 | Noel et al. |
| 5,540,796 A | 7/1996 | Fries |
| 5,562,650 A | 10/1996 | Everett et al. |
| 5,595,618 A | 1/1997 | Fries et al. |
| 5,669,894 A * | 9/1997 | Goldman et al. ............ 604/368 |
| 5,722,966 A * | 3/1998 | Christon et al. ............ 604/364 |
| 5,770,528 A * | 6/1998 | Mumick et al. ............... 442/59 |
| 5,904,675 A | 5/1999 | Laux et al. |
| 5,972,265 A | 10/1999 | Marra et al. |
| 5,990,377 A * | 11/1999 | Chen et al. .................. 604/381 |
| 6,235,966 B1 * | 5/2001 | Magnusson et al. ......... 604/374 |
| 6,492,574 B1 * | 12/2002 | Chen et al. .................. 604/378 |

\* cited by examiner

```
Cambridge Instruments  QUANTIMET 970  QUIPS/MX: V08.00      USER :

DISTRIBUTION OF  PERCAREA  vs FIELDNUM

Total PERCAREA  =  3109.48 Mean =   51.7  Std Dev =  27.2
              Undersize Count =      0.  Oversize Count =      6.

FIELDNUM   (##         )
  LIMITS     PERCAREA  PERCENT
    0.         0.        0.00 :
    3.00       0.130719  0.00 :
    6.00       3.071895  0.10 :
    9.00      50.588240  1.73 :
   12.00      56.928110  3.56 :1
   15.00      29.346410  4.50 :1
   18.00      40.130720  5.80 :11
   21.00      37.581700  7.00 :11
   24.00      34.836600  8.12 :111
   27.00      52.810460  9.82 :111
   30.00      44.836610 11.26 :1111
   33.00      44.967320 12.71 :1111
   36.00      43.594780 14.11 :11111
   39.00      49.687840 15.71 :11111
   42.00      44.575170 17.14 :111111
   45.00      48.169940 18.69 :1111111
   48.00      35.359480 19.83 :1111111
   51.00      34.836600 20.95 :1111111
   54.00      35.620920 22.09 :11111111
   57.00      38.692820 23.34 :11111111
   60.00      52.222220 25.02 :11111111
   63.00      44.705880 26.46 :111111111
   66.00      33.660130 27.54 :111111111
   69.00      43.856210 28.95 :1111111111
   72.00      36.862750 30.13 :1111111111
   75.00      50.326800 31.75 :11111111111
   78.00      41.568630 33.09 :11111111111
   81.00      43.202610 34.48 :111111111111
   84.00      71.633990 36.78 :111111111111
─ 87.00      56.928110 38.61 :1111111111111
   90.00      74.509810 41.01 :1111111111111
   93.00      74.648520 43.41 :11111111111111
   96.00     132.614400 47.67 :111111111111111
   99.00     167.124200 53.05 :11111111111111111
  102.00     116.339900 56.79 :111111111111111111
  105.00      91.568630 59.74 :1111111111111111111
─108.00     101.764700 63.01 :11111111111111111111
  111.00      94.705890 66.05 :11111111111111111111
  114.00      71.830070 68.36 :111111111111111111111
  117.00      59.150330 70.27 :1111111111111111111111
  120.00      49.542480 71.86 :1111111111111111111111
  123.00      50.065360 73.47 :11111111111111111111111
  126.00      46.797390 74.97 :11111111111111111111111
  129.00      48.758170 76.54 :111111111111111111111111
  132.00      46.666670 78.04 :111111111111111111111111
  135.00      50.326800 79.66 :1111111111111111111111111
  138.00      52.222230 81.34 :1111111111111111111111111
  141.00      49.934640 82.95 :11111111111111111111111111
  144.00      50.196080 84.56 :11111111111111111111111111
  147.00      57.973860 86.43 :111111111111111111111111111
  150.00      56.993470 88.26 :111111111111111111111111111
  153.00      40.915040 89.57 :1111111111111111111111111111
  156.00      43.660130 90.98 :1111111111111111111111111111
  159.00      50.065360 92.59 :11111111111111111111111111111
  162.00      28.366010 93.50 :11111111111111111111111111111
  165.00      25.163400 94.31 :11111111111111111111111111111
  168.00      35.294120 95.45 :111111111111111111111111111111
  171.00      28.235300 96.35 :111111111111111111111111111111
  174.00      50.522880 97.98 :111111111111111111111111111111
  177.00      36.470590 99.15 :1111111111111111111111111111111
  180.00      20.653600 99.82 :1111111111111111111111111111111
```

FIG. 9A

Cambridge Instruments QUANTIMET 970 QUIPS/MX: V08.00     USER :

DISTRIBUTION OF PERCAREA vs FIELDNUM

Total PERCAREA = 3303.14 Mean = 54.7  Std Dev = 17.0
          Undersize Count =    0.  Oversize Count =    21.

```
FIELDNUM   (#)
 LIMITS     PERCAREA   PERCENT
    0.         0.        0.00 :
    3.00     28.039220   0.85 :
    6.00     61.830060   2.72 :1
    9.20     39.084970   3.90 :1
   12.00     52.091500   5.48 :11
   15.00     44.313730   6.82 :11
   18.00     56.143790   8.52 :111
   21.00     61.895430  10.40 :111
   24.00     60.915040  12.24 :1111
   27.00     52.614380  13.83 :11111
   30.00     46.535940  15.24 :11111
   33.00     51.307200  16.80 :111111
   36.00     35.620920  17.87 :111111
   39.00     52.026150  19.45 :1111111
   42.00     44.183010  20.79 :1111111
   45.00     27.124180  21.61 :1111111
   48.00     42.679740  22.90 :11111111
   51.00     46.535950  24.31 :11111111
   54.00     65.424840  26.29 :111111111
   57.00     54.967320  27.95 :111111111
   60.00     56.797390  29.67 :1111111111
   63.00     48.300660  31.13 :1111111111
   66.00     45.620910  32.52 :11111111111
   69.00     54.575170  34.17 :11111111111
   72.00     51.699350  35.73 :111111111111
   75.00     43.856220  37.06 :111111111111
   78.00     53.137260  38.67 :1111111111111
 - 81.00     98.130720  41.40 :1111111111111
   84.00     60.261440  43.22 :11111111111111
   87.00     89.477130  45.93 :111111111111111
   90.00     81.111120  48.39 :1111111111111111
   93.00     60.326800  50.21 :1111111111111111
   96.00     90.        52.94 :11111111111111111
   99.00     83.529420  55.47 :11111111111111111
 -102.00    107.124200  58.71 :111111111111111111
  105.00     60.326800  60.54 :1111111111111111111
  108.00     57.647060  62.28 :1111111111111111111
  111.00     74.785890  64.54 :11111111111111111111
  114.00     75.751630  66.84 :111111111111111111111
  117.00     55.163400  68.51 :111111111111111111111
  120.00     22.810460  69.20 :1111111111111111111111
  123.00     42.091510  70.47 :1111111111111111111111
  126.00     57.647060  72.22 :11111111111111111111111
  129.00     70.588240  74.35 :11111111111111111111111
  132.00     75.832690  76.63 :111111111111111111111111
  135.00     78.039220  78.99 :1111111111111111111111111
  138.00     49.869280  80.50 :1111111111111111111111111
  141.00     28.692820  81.37 :11111111111111111111111111
  144.00     40.653600  82.60 :11111111111111111111111111
  147.00     49.084970  84.08 :111111111111111111111111111
  150.00     44.313730  85.42 :111111111111111111111111111
  153.00     63.071890  87.33 :1111111111111111111111111111
  156.00     41.699350  88.60 :1111111111111111111111111111
  159.00     41.633990  89.86 :11111111111111111111111111111
  162.00     57.124190  91.59 :11111111111111111111111111111
  165.00     41.503270  92.84 :111111111111111111111111111111
  168.00     38.496740  94.01 :111111111111111111111111111111
  171.00     35.424840  95.08 :1111111111111111111111111111111
  174.00     37.777780  96.22 :1111111111111111111111111111111
  177.00     50.        97.74 :11111111111111111111111111111111
  180.00     53.529410  99.36 :11111111111111111111111111111111
```

FIG. 10A

Cambridge Instruments QUANTIMET 970 QUIPS/MX: V08.00      USER :

DISTRIBUTION OF PERCAREA vs FIELDNUM

Total PERCAREA =  3565.49 Mean =   59.3  Std Dev = 14.9
        Undersize Count =      0.  Oversize Count =    26.

```
FIELDNUM  (##      )
  LIMITS      PERCAREA    PERCENT
    0.          0.          0.00 :
    3.00        7.320262    0.21 :
    6.00       87.581700    2.66 :1
    9.00       48.562100    4.02 :1
   12.00       44.313730    5.27 :11
   15.00       44.771240    6.52 :11
   18.00       43.921570    7.75 :11
   21.00       48.000000    8.88 :111
   24.00       44.967320   10.14 :111
   27.00       58.823530   11.79 :1111
   30.00       56.862750   13.38 :11111
   33.00       64.117660   15.18 :11111
   36.00       42.352940   16.37 :111111
   39.00       25.098040   17.07 :111111
   42.00       52.941180   18.56 :1111111
   45.00       60.718950   20.26 :1111111
   48.00       61.307190   21.98 :11111111
   51.00       65.882350   23.83 :11111111
   54.00       71.633990   25.84 :111111111
   57.00       68.823530   27.77 :111111111
   60.00       53.137260   29.26 :1111111111
   63.20       62.222220   31.00 :1111111111
   66.00       74.771240   33.10 :11111111111
   69.00       57.843150   34.72 :11111111111
   72.00       71.372550   36.72 :11111111111
   75.00       56.928110   38.32 :111111111111
   78.00       75.359480   40.43 :111111111111
   81.00       86.013070   42.85 :1111111111111
 — 84.00       85.947710   45.26 :11111111111111
   87.00       40.522880   46.39 :11111111111111
   90.00       76.078430   48.53 :111111111111111
   93.00       74.117660   50.60 :111111111111111
   96.00       68.496740   52.53 :1111111111111111
 — 99.00       43.006530   53.73 :1111111111111111
  102.00       60.849680   55.44 :11111111111111111
  105.00       62.875820   57.20 :11111111111111111
  108.00       65.555560   59.04 :111111111111111111
  111.00       47.254900   60.37 :111111111111111111
  114.00       64.052290   62.16 :1111111111111111111
  117.00       53.398690   63.66 :1111111111111111111
  120.00       53.071890   65.15 :11111111111111111111
  123.00       58.496730   66.79 :11111111111111111111
  126.00       60.653600   68.49 :111111111111111111111
  129.00       58.954250   70.14 :111111111111111111111
  132.00       56.470590   71.73 :1111111111111111111111
  135.00       41.437910   72.89 :1111111111111111111111
  138.00       53.856210   74.40 :11111111111111111111111
  141.00       61.176470   76.12 :11111111111111111111111
  144.00       88.627460   78.60 :111111111111111111111111
  147.00       74.640530   80.70 :1111111111111111111111111
  150.00       68.954250   82.63 :1111111111111111111111111
  153.00       58.431370   84.27 :11111111111111111111111111
  156.00       59.673210   85.94 :11111111111111111111111111
  159.00       77.973860   88.13 :111111111111111111111111111
  162.00       74.705880   90.22 :111111111111111111111111111
  165.00       48.235300   91.58 :1111111111111111111111111111
  168.00       68.300650   93.49 :1111111111111111111111111111
  171.00       48.235300   94.85 :11111111111111111111111111111
  174.00       50.588240   96.26 :11111111111111111111111111111
  177.00       64.901960   98.08 :111111111111111111111111111111
  180.00       41.960790   99.26 :111111111111111111111111111111
```

FIG. 11A

HIGH-STRENGTH, STABILIZED ABSORBENT ARTICLE

FIELD OF THE INVENTION

The present invention relates to absorbent structures, such as those employed in infant diapers, childcare training pants, adult incontinence products, feminine hygiene products, and the like. More particularly, the present invention relates to absorbent articles having improved combinations of high absorbency and high strength with increased stability.

BACKGROUND OF THE INVENTION

Absorbent structures composed of superabsorbent particles and cellulosic wood pulp fibers have been employed in conventional absorbent products. Absorbent structures which include multiple layers have also been employed in conventional absorbent products.

In conventional absorbent articles, however, the absorbent structures undergo significant mechanical stress during ordinary use. The absorbent structure can break into multiple segments, or parts of the absorbent structure can shift and move to undesired locations. The in-use dynamics and stresses can frequently cause the absorbent structures to crack, break, rope and slump. When thin absorbent structures are employed, the tendency to slump, crack, break, and/or rope can increase. As a result of the mechanical degradation of the absorbent structure, the absorption characteristics of the absorbent structure degrade. The transport of liquids through the absorbent structure can be impeded, and the leakage of waste materials from the absorbent structure can become excessive. For example, breakage can typically occur along the fold lines imparted for packaging the absorbent products. Where an absorbent structure breaks along a crotch fold line, the rear portion of the absorbent product can become isolated and become substantially unavailable for the absorption of liquids. When the front portion of the product becomes saturated, the product can prematurely leak without utilizing its entire absorbent capacity.

To improve the mechanical integrity of conventional absorbent structures, adhesives have been mixed or otherwise applied to the absorbent fibers. For example, absorbent structures have been stabilized by applying a hot melt adhesive powder agent. Other absorbent structures have been modified by adding a binder material. Still other conventional configurations have employed layers of tissue to wrap the absorbent structure. Further configurations have employed a wet-strength tissue located in a middle region of the thickness of the absorbent structure.

Conventional absorbent structures or cores have been produced by employing various air laying processes, and the airlaid webs have typically been manufactured within a forming chamber. Binder materials or binder fibers have been introduced into the forming chamber for introduction onto the airlaid absorbent structure.

Conventional absorbent structures, such as those described above, have required excessive amounts of adhesive or other binder material to generate desired levels of integrity and wet-strength. In addition, the conventional absorbent structures have not exhibited the desired combinations of softness, low cost, high absorbency rate, low stiffness, and high strength and stability. As a result, there has been a continued need for absorbent structures having improved combinations of wet-integrity and high absorbency.

BRIEF DESCRIPTION OF THE INVENTION

The present invention provides an absorbent article comprising a backsheet layer, a liquid permeable topsheet layer, and an absorbent body sandwiched between the backsheet layer and topsheet layer. The absorbent body includes a first fibrous stratum having a first quantity of absorbent fibers, a second fibrous stratum having a second quantity of absorbent fibers, and at least a third fibrous stratum which is located between and integrally formed with the first and second fibrous strata. The third fibrous stratum includes a third quantity of absorbent fibers. In particular aspects, the third fibrous stratum includes an operative quantity of a substantially hydrophilic, wet-strength agent which is distributed in the third quantity of absorbent fibers. In other aspects, the wet-strength agent can render the third fibrous stratum substantially non-dispersible.

In it's various aspects and configurations, the present invention can provide an absorbent structure having an improved combination of softness, low cost and rapid uptake of absorbed liquids. In desired aspects, the invention can provide an improved distribution of absorbed liquid between the various strata of the absorbent structure. In addition, the invention can provide a stabilized absorbent structure which has increased resistance to cracking, breaking, bunching, roping and/or twisting. In desired configurations, the stabilized absorbent structure can exhibit less surface staining, can provide improved distributions of liquid along the length and width of the absorbent structure, and can provide reduced leakage.

BRIEF DESCRIPTION OF THE DRAWINGS

The present invention will be more fully understood and further advantages will become apparent when reference is made to the following detailed description of the invention and the drawings, in which:

FIG. 9A shows a representative histogram of the observed distribution of "percent area" generated from a specimen of the type representatively shown in FIG. 9;

FIG. 10A shows a representative histogram of the observed distribution of "percent area" generated from a specimen of the type representatively shown in FIG. 10;

FIG. 11A shows a representative histogram of the observed distribution of "percent area" generated from a specimen of the type representatively shown in FIG. 11;

DETAILED DESCRIPTION OF THE INVENTION

Figure 1:
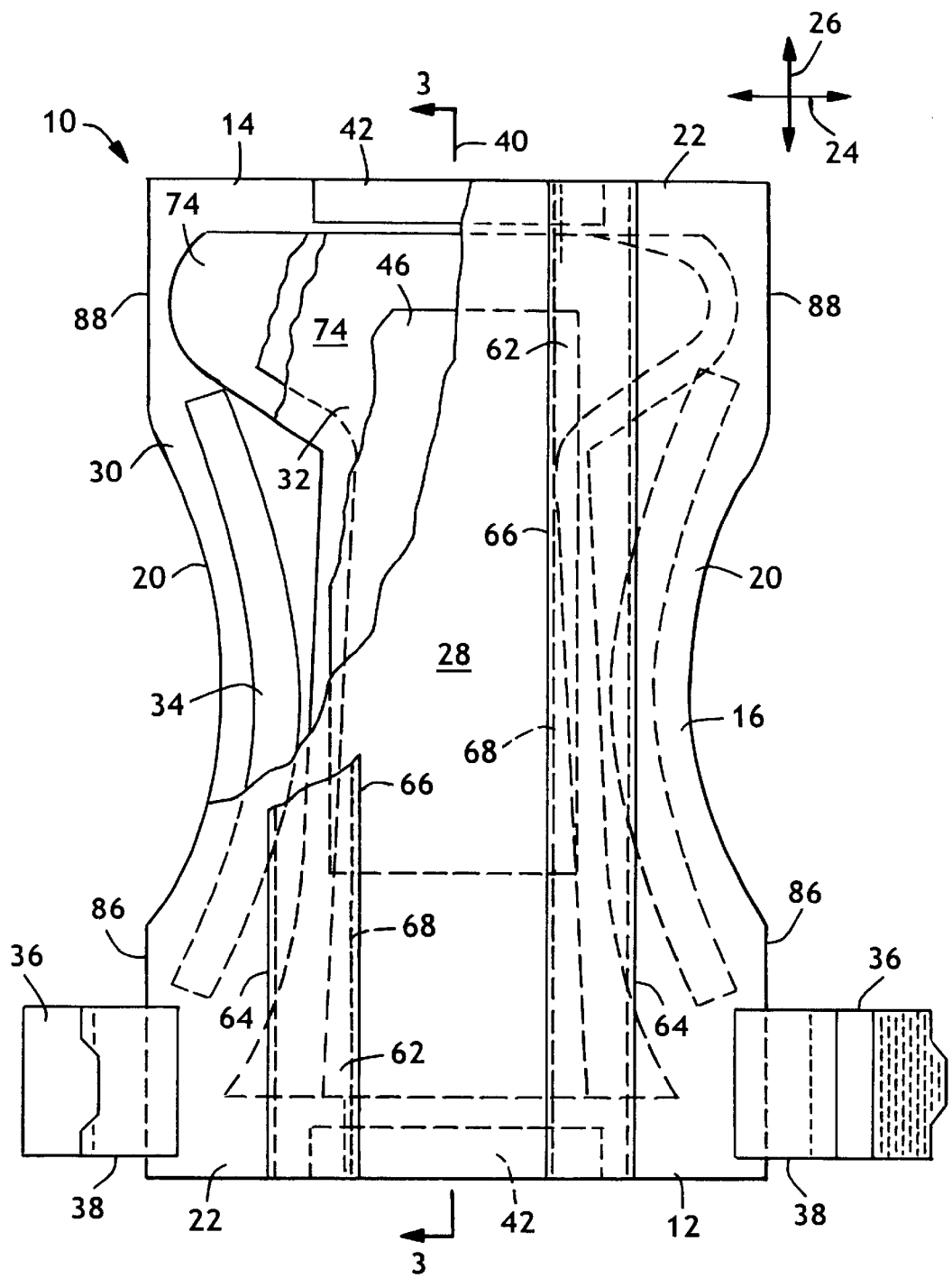
FIG. 1 representatively shows a schematic, top plan view of an inward side of an absorbent article which incorporates the absorbent structures of the invention.

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

With reference to FIGS. 1, 2, 3 and 4, an absorbent article, such as diaper 10, includes a backsheet layer 30, a liquid permeable topsheet layer 28 and an absorbent body member 32 which is sandwiched between the backsheet layer 30 and topsheet layer 28. The absorbent body includes a first fibrous stratum 52 having a first quantity of absorbent fibers, a second fibrous stratum 54 having a second quantity of absorbent fibers, and at least an intermediate, third fibrous stratum 56. The third fibrous stratum includes a third quantity of absorbent fibers, and is located between the first and second fibrous strata. The intermediate fibrous stratum is integrally formed with at least the first fibrous stratum, and desirably, is integrally formed with both the first and second fibrous strata. In particular aspects, the third fibrous stratum 56 also includes an operative quantity of a substantially hydrophilic, wet-strength agent which is distributed in the third quantity of absorbent fibers. In other aspects, the wet-strength agent can render the third fibrous stratum 56 substantially non-dispersible. Preferably, the third fibrous stratum is substantially non-dispersible in an aqueous liquid.

In a desired aspect, the third fibrous stratum includes a relatively greatest amount of wet-strength agent, as compared to the first and second fibrous strata. A more particular aspect of the invention can include first and/or second fibrous strata 52 and 54 which are substantially free of the wet-strength agent. In another aspect, the first and/or second fibrous strata are substantially dispersible in a selected liquid. Preferably, the first and/or second fibrous strata are substantially dispersible in an aqueous liquid. A further aspect of the invention can provide a configuration wherein the structure of the absorbent body 32 provides a remainder basis weight which is substantially non-dispersible in the selected liquid (e.g. aqueous liquid), and the remainder basis weight is at least about 30 g/m$^2$. In still other aspects, the intermediate fibrous stratum can include an amount of wet-strength agent which is not more than about 1 wt % of the overall absorbent body.

In it's various aspects and configurations, the present invention can provide an absorbent core structure having high-strength and low density. In particular aspects, an appointed body side layer, such as the second fibrous stratum 54 can have a low density to provide improved softness and more rapid uptake of liquids. In other aspects, a low density outward side surface portion, such as provided by the first fibrous stratum 52, can also provide softness and resilience. Where the intermediate, third fibrous stratum 56 is integrally formed and connected between the first and second fibrous strata, the absorbent body structure 32 can provide increased wet-strength along with an improved ability to distribute liquid between the various strata of the absorbent body. The third fibrous stratum 56, can help provide a stabilized absorbent body 32 which has increased resistance to cracking, breaking, bunching, roping and/or twisting even after the absorbent has been wetted. Additionally, the stabilized absorbent body 32 can exhibit greater resistance to side compression. The stabilized absorbent body can also exhibit less surface staining, provide improved distributions of liquid along the length and width (x-y directions) of the absorbent structure, and provide reduced leakage.

A suitable method and apparatus for making an absorbent web material that can be employed to construct the absorbent body 32 are described in copending U.S. patent application Ser. No. 09/631,492 entitled PROCESS AND APPARATUS FOR FORMING A STABILIZED ABSORBENT WEB by A. J. Wisneski et al., which was contemporaneously filed Aug. 3, 2000; and copending U.S. patent application Ser. No. 09/632,253 entitled MULTI-CHAMBER PROCESS AND APPARATUS FOR FORMING A STABILIZED ABSORBENT WEB by A. J. Wisneski et al., which was contemporaneously filed Aug. 3, 2000. The entire disclosures of these documents are incorporated herein by reference in a manner that is consistent (not in contradiction) herewith.

The article of the invention can, for example, be a garment provided by the representatively shown disposable diaper 10. In desired configurations, the article can provide a first waistband portion, such as the shown back waistband portion 12, and a second waistband portion, such as the shown front waistband portion 14. The article can additionally have an intermediate or crotch portion 16 which interconnects between the first and second waistband portions 12 and 14, respectively. The article can further include a backsheet layer 30, a liquid permeable topsheet layer 28 connected and assembled in facing relation with the backsheet layer, and an absorbent structure, such as a structure which includes absorbent body 32. The absorbent structure is sandwiched between the backsheet and topsheet layers, and is operably held therebetween. An operative fastening system, such as the shown system having fasteners 36, is typically constructed and arranged to interconnect the first waistband portion 12 with the second waistband portion 14 to hold the article on a wearer. The fastening system can be operatively configured to join the first, back waistband portion 12 in an overlapping relation with the second, front waistband portion 14 in a back-to-front arrangement to thereby encircle the wearer's body and hold the diaper secure on the wearer during use. Optionally, the fastening system can employ fasteners 36 which are configured to join the front waistband portion 14 in an overlapping relation with the back waistband portion 12 in a front-to-back arrangement to secure the diaper. In such optional arrangements, the front waistband region may be identified as the first waistband portion and the rear waistband region may be identified as the second waistband portion.

The front waistband section 14 of the representatively shown diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article can also have an appointed fastener landing zone member 50 which is disposed on the outward surface of the article. In the configuration shown in FIGS. 1 and 2, for example, the landing member 50 can be disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

Figure 2:
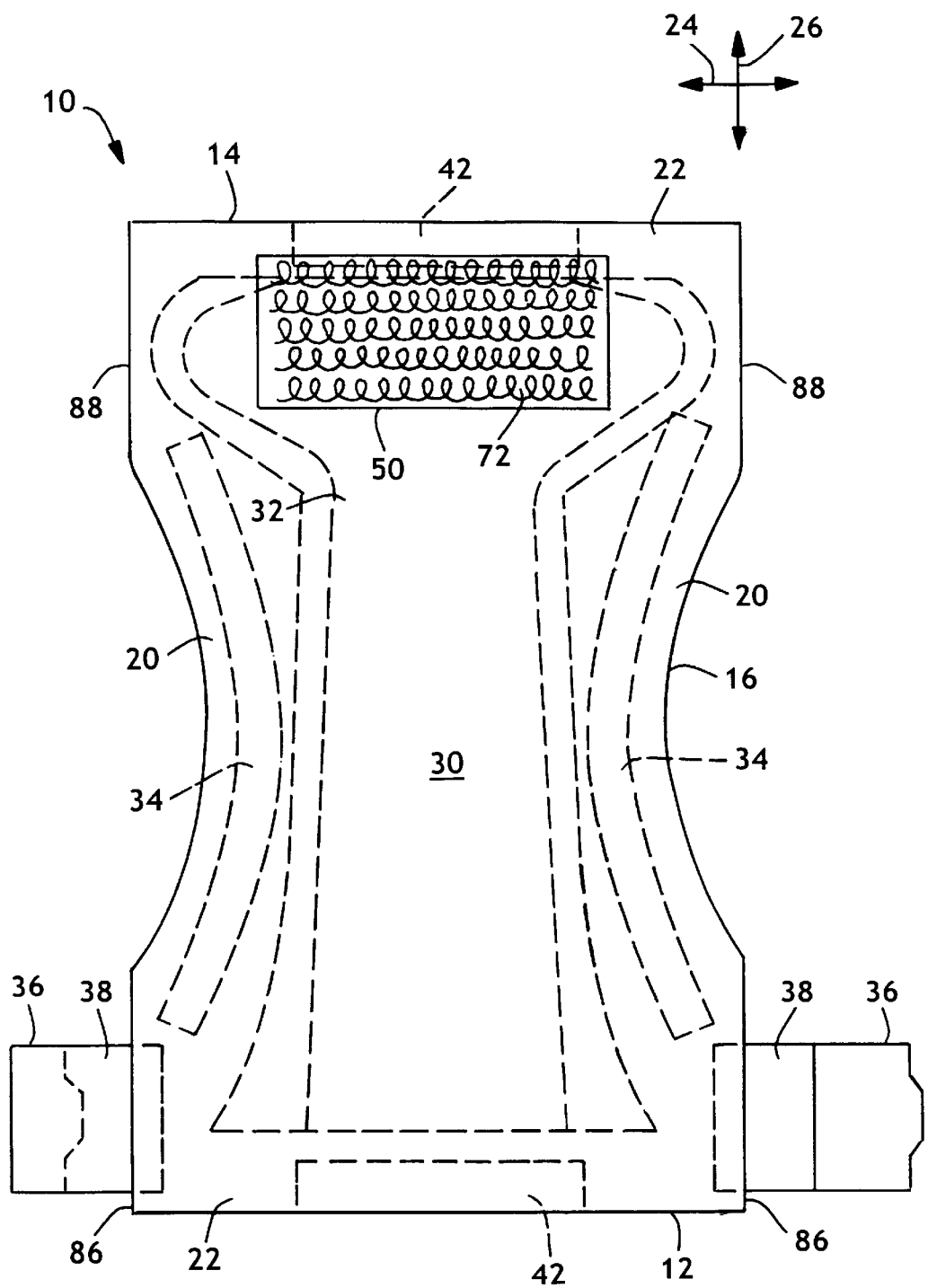
FIG. 2 representatively shows a schematic, top plan view of an outward side of an absorbent article which incorporates the absorbent structures of the invention.

FIGS. 1 and 2 show typical plan views of the representative disposable diaper 10 in its generally flat-out, uncontracted state (i.e., with substantially all elastic induced gathering and contraction removed). In FIG. 1, portions of the structure are partially cut away to more clearly show the interior construction of the diaper article, and the bodyside surface of the diaper which contacts the wearer is facing the viewer. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article are configured to face away from the wearer's body when the article is placed about the wearer.

Figure 3:
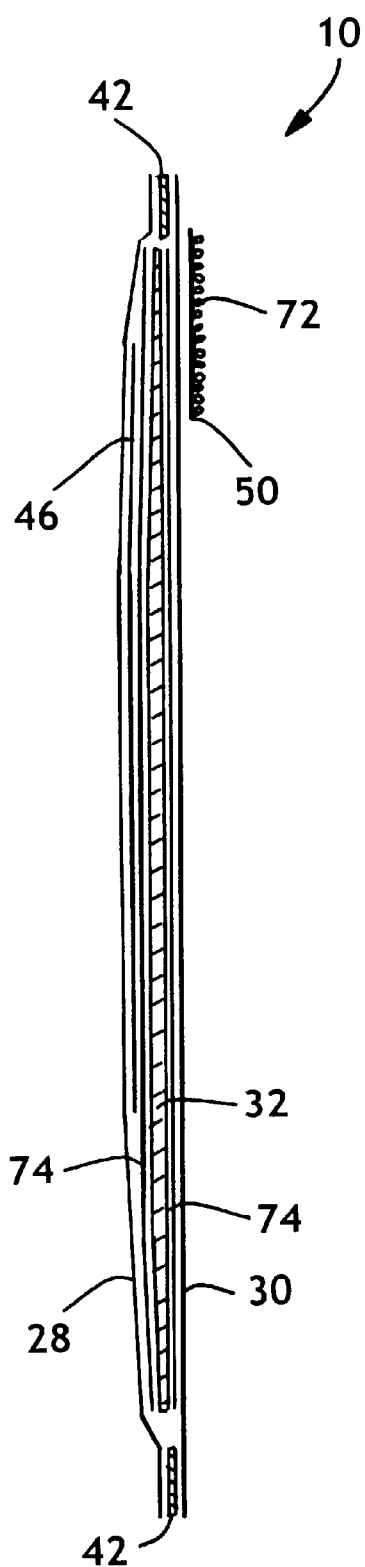
FIG. 3 representatively shows a longitudinal, cross-sectional, side view taken along line 3—3 of FIG. 1.

With reference to FIGS. 1, 2 and 3, the diaper 10 can typically include a porous, liquid permeable topsheet 28; a substantially liquid impermeable backsheet 30; an absorbent body structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with an appointed storage or retention portion of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993. Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995; in U.S. Pat. No. 5,540,796 entitled A PROCESS FOR ASSEMBLING ELASTICIZED EAR PORTIONS by D. Fries, which issued Jul. 30, 1996; and in U.S. Pat. No. 5,595,618 entitled AN ASSEMBLY PROCESS FOR A LAMINATED TAPE by D. Fries, which issued Jan. 21, 1997. The disclosures of the above-described documents are incorporated herein by reference in a manner that is consistent (not in conflict) herewith.

The diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated fluid surges typically occur in the diaper or other disposable absorbent article.

The backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present disclosure, the term "flexible" refers to materials which are compliant and which will readily conform to the general shape and contours of the wearer's body. Backsheet 30 prevents the exudates contained in absorbent body 32 from wetting articles, such as bedsheets and overgarments, which contact diaper 10. In particular embodiments of the invention, backsheet 30 can include a film, such as a polyethylene film, having a thickness of from about 0.012 millimeters (0.5 mil) to about 0.051 millimeters (2.0 mil). For example, the backsheet film can have a thickness of about 0.032 millimeters (1.25 mil).

Alterative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, non-woven fabric layer laminated to an appointed facing surface of a polymer film layer which may or may not be gas-permeable. Ordinarily, the fabric layer is attached to an outward facing surface of the polymer film layer. Other examples of fibrous, cloth-like backsheet materials can comprise a stretch-thinned or a stretch-thermal-laminate material composed of a 0.6 mil (0.015 mm) thick polypropylene blown film and a 0.7 ounce per square yard (23.8 g/m$^2$) polypropylene spunbond material (2 denier fibers).

In particular arrangements, a substantially liquid impermeable, vapor permeable backsheet layer may be a composite material which includes a vapor permeable film layer adhesively laminated to a spunbond layer. The vapor permeable film layer can be obtained from Exxon Chemical Products Incorporated, under the tradename EXXAIRE. The film layer can include 48–60 weight percent (wt %) linear low density polyethylene and 38–50 wt % calcium carbonate particulates which may be uniformly dispersed and extruded into the film layer. The stretched film layer can have a thickness of about 0.7 mil (about 0.018 mm) and a basis weight of 16–22 grams per square meter (g/m$^2$). The spunbond layer can be adhesively laminated to the film layer, and can have a basis weight of about 27 g/m$^2$. The spunbond layer can be made using conventional spunbond technology, and can include filaments of polypropylene having a fiber denier of 1.5–3 dpf. The vapor-permeable film layer may be adhered to the spunbond layer using a pressure sensitive, hot melt adhesive at an add-on rate of about 1.6 g/m$^2$, and the adhesive can be deposited in the form of a pattern of adhesive swirls or a random fine fiber spray.

The liquid impermeable, vapor permeable backsheet layer may alternatively include a highly breathable stretch thermal laminate material (HBSTL). The HBSTL material can include a polypropylene spunbond material thermally attached to a stretched breathable film. For example, the HBSTL material may include a 0.6 osy (20.4 g/m$^2$) polypropylene spunbond material thermally attached to a 18.7 g/m$^2$ stretched breathable film. The breathable film may include two skin layers with each skin layer composed of 1–3 wt % EVA/catalloy. The breathable film may also include 55–60 wt % calcium carbonate particulates, linear low density polyethylene, and up to 4.8% low density polyethylene. The stretched breathable film can include a thickness of 0.45–0.50 mils (0.011–0.013 mm) and a basis weight of 18.7 g/m$^2$. The spunbond layer can be thermally bonded to the breathable film, and can have a basis weight of about 20.4 g/m$^2$. The spunbond layer can have a fiber denier of 1.5–3 dpf, and the stretched breathable film can be thermally attached to the spunbond material using a "C-star" pattern which provides an overall bond area of 15–20%.

The various types of such materials have been employed to form the backsheet or outercover of HUGGIES disposable diapers, which are commercially available from Kimberly-Clark Corporation. The backsheet 30 typically provides the outer cover of the article. Optionally, however, the article may include a separate outer cover component member which is additional to the backsheet. The backsheet may also be embossed or otherwise provided with a pattern or matte finish to exhibit a more aesthetically pleasing appearance.

As mentioned, the backsheet 30 may include a microporous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. Another example of a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn.

In the various configurations of the invention, where a component such as the backsheet 30 or the containment flaps 62 are configured to be permeable to gas while having a resistance and limited permeability to aqueous liquid, the liquid resistant material can have a construction which is capable of supporting a selected hydrohead of water substantially without leakage therethrough. For example, desired materials can support a hydrohead of at least about 45 cm of water substantially without leakage therethrough. A suitable technique for determining the resistance of a material to liquid penetration is Federal Test Method Standard FTMS 191 Method 5514, 1978, or an equivalent thereof.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1 inch), to provide at least a portion of the side and/or end margins.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% TRITON X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment mechanisms may also be employed to suitably interconnect, assemble and/or affix together the various other component parts of the articles which are described herein.

The absorbent body 32 provides an absorbent structure which can include a retention portion, such as the representatively shown absorbent pad composed of selected hydrophilic fibers and high-absorbency particles, for holding and storing absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials are typically xerogels which form hydrogels when wetted. The term "hydrogel", however, has commonly been used to also refer to both the wetted and unwetted forms of the material.

As mentioned previously, the high-absorbency material used in the absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent body 32. Desired for use are particles having an average size of from about 20 micrometers to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, the absorbent system can include an overwrap, such as wrap sheet 74, which is placed immediately adjacent and around the absorbent body 32 and may be bonded to the absorbent body and to various other components of the article. The wrap sheet can desirably be liquid permeable, and can be a layer of absorbent material which covers the major bodyside and outerside surfaces of the absorbent body. In desired configurations, the wrap sheet can operatively enclose substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of the absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of the absorbent body 32. Such a configuration of the wrap sheet can, for example, facilitate the formation of a substantially complete sealing and closure around the peripheral edges of the absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of the absorbent wrap 74 can extend at least about 0.5 inch (about 1.27 cm) beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of the wrap sheet 74 may be composed of substantially the same material, or may be composed of different materials. For example, the outerside layer of the wrap sheet may be composed of a relatively lower basis weight material having a relatively high porosity, such as a wet-strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

The diaper 10 can also include a surge management layer 46 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, the surge layer 46 can be located on an inwardly facing body side surface of the topsheet layer 28. Alternatively, the surge layer 46 may be located adjacent to an outer side surface of the topsheet 28. Accordingly, the surge layer would then be interposed between the topsheet 28 and the absorbent body 32. Examples of suitable surge management layers 46 are described in U.S. Pat. No. 5,486,166 entitled FIBROUS NONWOVEN WEB SURGE LAYER FOR PERSONAL CARE ABSORBENT ARTICLES AND THE LIKE by C. Ellis and D. Bishop, which issued Jan. 23, 1996; and U.S. Pat. No. 5,490,846 entitled IMPROVED SURGE MANAGEMENT FIBROUS NONWOVEN WEB FOR PERSONAL CARE ABSORBENT ARTICLES AND THE LIKE by C. Ellis and R. Everett, which issued Feb. 13, 1996; the entire disclosures of which are hereby incorporated by reference in a manner that is consistent herewith.

The leg elastic members 34 are located in the lateral side margins 20 of diaper 10, and are arranged to draw and hold diaper 10 against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10.

Alternatively, elastic members 34 may extend the entire length of diaper 10, or any other length suitable for providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (e.g. FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 by T. Wisneski et al. which issued May 5, 1987, the entire disclosure of which is hereby incorporated by reference in a manner that is consistent herewith. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference in a manner that is consistent herewith. Examples of NBL materials are described in U.S. Pat. No. 5,226,992 by Mormon which issued Jul. 13, 1993, the entire disclosure of which is hereby incorporated by reference in a manner that is consistent herewith.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 by P. VanGompel et al. which issued Jul. 3, 1990, the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30. Additionally, a second pair of ear regions may be included to extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

Diaper 10 can also include a pair of elasticized containment flaps 62 which extend generally length-wise along the longitudinal direction 26 of the diaper. The containment flaps are typically positioned laterally inboard from the leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 by K. Enloe which issued Nov. 3, 1987, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. Pat. No. 5,562,650 entitled ABSORBENT ARTICLE HAVING AN IMPROVED SURGE MANAGEMENT by R. Everett et al., which issued Feb. 13, 1996, the disclosure of which is hereby incorporated by reference in a manner that is consistent herewith.

In optional, alternative configurations of the invention, diaper 10 may include internal, elasticized, containment waist flaps, such as those described in U.S. Pat. No. 4,753,646 issued Jun. 28, 1988, to K. Enloe; and in U.S. Pat. No. 5,904,675 entitled AN ABSORBENT ARTICLE WITH IMPROVED ELASTIC MARGINS AND CONTAINMENT SYSTEM by D. Laux et al., which issued May 18, 1999; the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, diaper 10 can include one or more, appointed landing member regions or patches, such as provided by the representatively shown, primary landing member 50. The landing member can provide an operable target area for generating a releasable and re-attachable securement with at least one of the fastener tabs 36. In desired embodiments of the invention, the landing member patch can be positioned on the front waistband portion 14 of the diaper and located on the outward surface of the backsheet layer 30. Alternatively, the landing member patch can be positioned on an appointed inward surface of the diaper, such as the bodyside surface of the topsheet layer 28.

Particular arrangements of the invention can include one or more landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the landing member may be composed of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 24.

The various configurations of the invention can include at least one separately provided fastener tab 36 located at either or both of the lateral end regions 86 of the back waistband 12. Alternatively, the at least one separately provided fastener tab 36 can be located at either or both of the lateral end regions 88 of the front waistband 14. The representatively shown embodiment, for example, has a laterally opposed pair of the fastener tabs 36 with a one of the fastener tabs located at each of the distal side edges of the rear waistband 12. More particularly, each of the fasteners 36 is assembled and attached to project and extend from a corresponding, immediately adjacent ear region located at one of the opposed, lateral end regions 86 of the front waistband section 12.

The fastener tab 36 can have any operative shape. For example, the shape of the fastener tab may be rectangular, trapezoidal, sinusoidal, rectilinear, curvilinear or the like, as well as combinations thereof. The laterally outboard, terminal edge of the fastener tab may be rectilinear or curvilinear, and as representatively shown, the terminal edge may be contoured to provide a protruding finger tab region.

The fastener tab 36 can be composed of a substantially non-elastomeric material, such as polymer films or tapes, woven fabrics, nonwoven fabrics or the like, as well as combinations thereof. Optionally, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically inter-engage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems typically include attachment members having the form of a "hook" or hook-like, male component, and include a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 36, and can locate the cooperating, second fastener component on the appointed engagement surface of the appointed landing member 50. For example, with the representatively shown hook-and-loop fastener, the fastening component which is attached to the appointed mating or securing surface of the fastener tab 36 may include a hook type of mechanical engagement element, and the complementary fastening component, which is operably joined and attached to the appointed landing zone member 50 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 36, may include the loop type of mechanical fastening element; and the complementary, second fastening component, which is operatively joined and attached to the appointed landing zone member, can include the hook type of attachment members.

Figure 4:
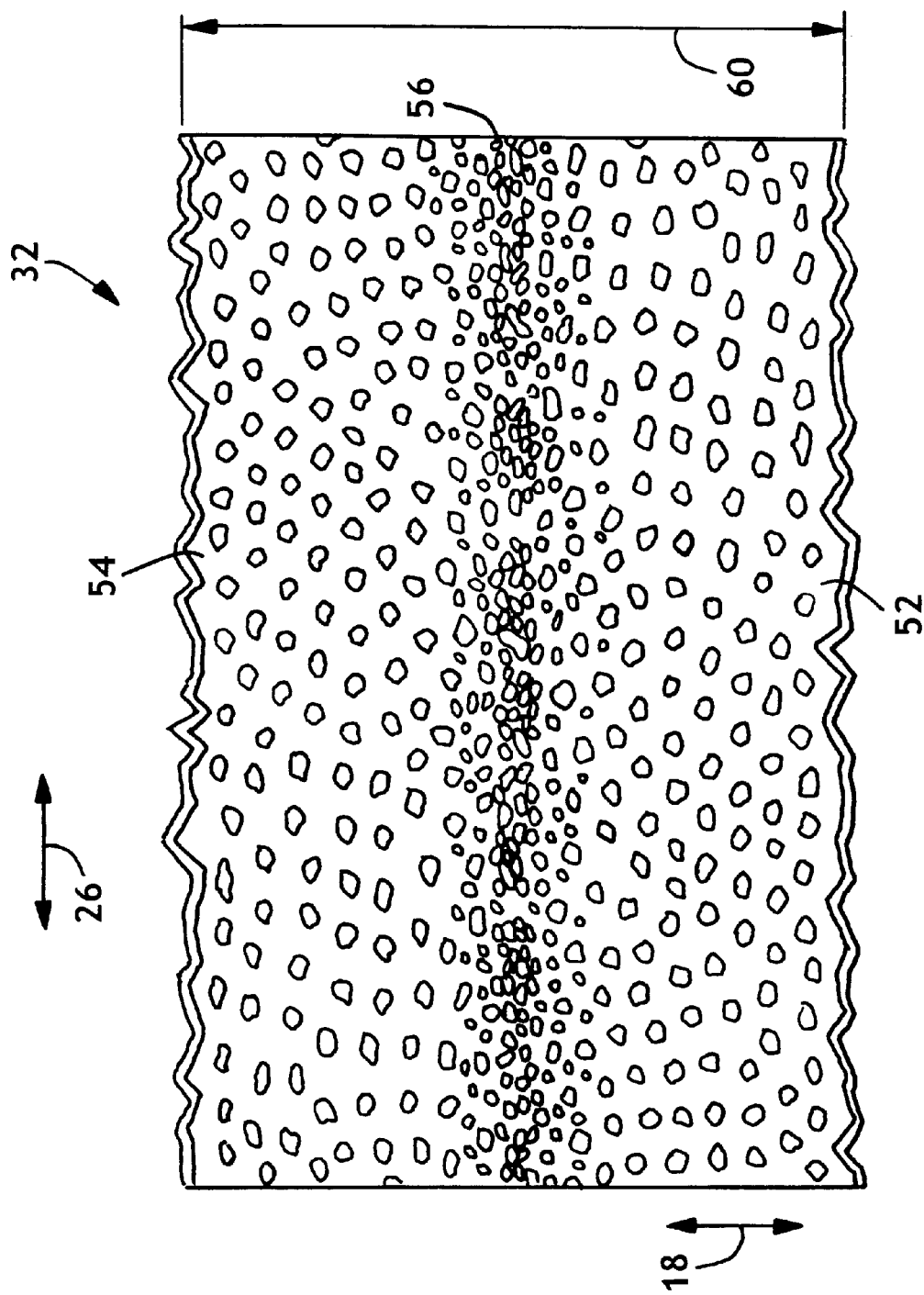
FIG. 4 representatively shows a schematic, enlarged, cross-sectional view of an absorbent body employed by the invention.
Figure 9:
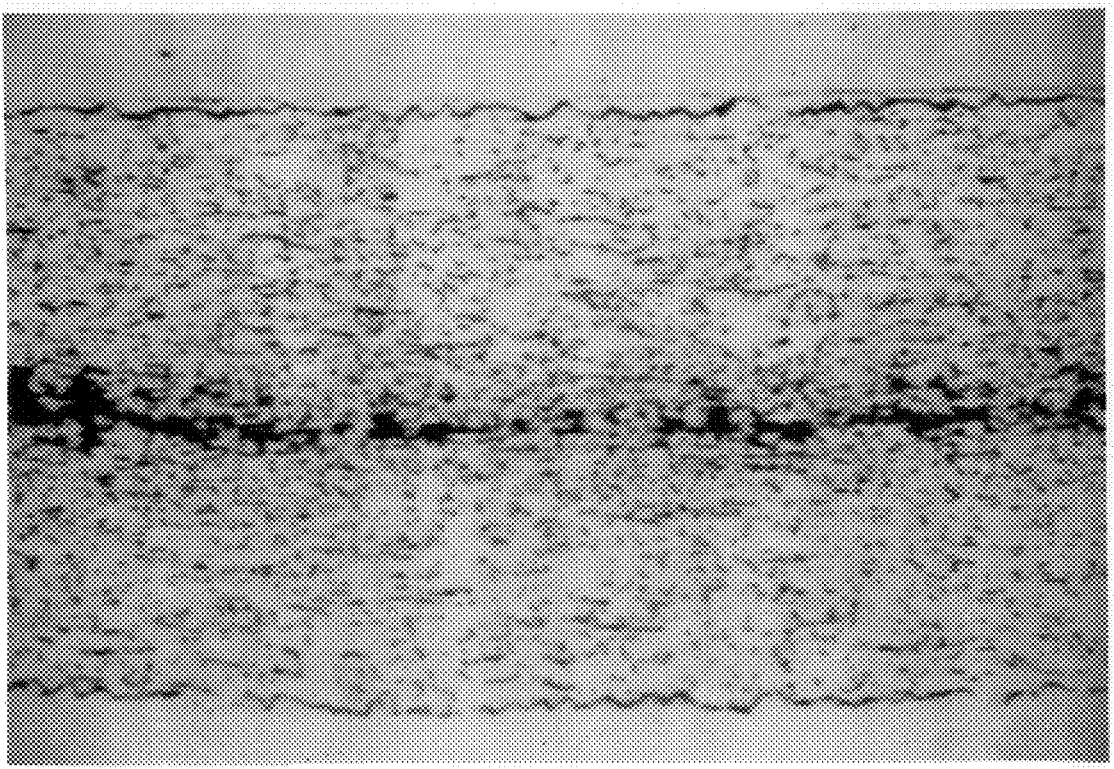
FIG. 9 representatively shows a photomicrograph of a thin-sectional specimen taken from a sample of an absorbent body of the invention which includes a stabilized intermediate layer.

With reference to FIGS. 4 and 9, the distribution of the wet-strength agent can be concentrated within a relatively thin region which is restricted to a limited portion of the z-directional, thickness dimension 18 of the absorbent body 32. In particular aspects, a thickness 58 of the intermediate, third fibrous stratum 56 can be a selected percentage of the overall thickness 60 of the absorbent body 32. In particular aspects, the third fibrous stratum thickness 58 can be at least a minimum of about 1 percent of the overall absorbent body thickness 60. The third fibrous stratum thickness can alternatively be at least about 5% of the overall absorbent body thickness, and optionally, can be at least about 10% of the overall absorbent body thickness to provide improved performance. In other aspects, the third fibrous stratum thickness can be not more than a maximum of about 80 percent of the overall absorbent body thickness 60. The third fibrous stratum thickness can alternatively be not more than about 50%, and optionally, can be not more than about 30% of the overall absorbent body thickness to provide improved effectiveness.

If the thickness 58 of the third fibrous stratum 56 is too large, the absorbent body 32 can be excessively stiff. If the thickness 58 of the third fibrous stratum 56 is too small, the absorbent body 32 can have insufficient strength, insufficient integrity, or an insufficient ability to spread and distribute liquids.

As representatively shown, the intermediate, third fibrous stratum 56 can be irregularly positioned between the first and second fibrous strata 52 and 54, respectively. Accordingly, the third fibrous stratum 56 and the first fibrous stratum 52 can have an irregular, diffuse interface therebetween. Additionally, the third fibrous stratum 56 and the second fibrous stratum 54 can have an irregular, diffuse interface therebetween.

The diffuse interface between the fibrous strata can extend substantially continuously along a portion of the thickness dimension of the absorbent body, particularly along at least a portion of the third fibrous stratum 56. The diffuse interface can also provide a distinctive concentration gradient of the wet-strength agent along the thickness dimension of the absorbent body, with the highest concentration of wet-strength agent located in a middle region of the third stratum 56 and relatively lower concentrations located in the regions encountered as one moves toward the first fibrous stratum 52 and/or second fibrous stratum 54. As a result, the diffuse interface can advantageously improve the distribution of liquids between the fibrous strata, and can help provide an increased rate of liquid absorption into the absorbent body 32.

In particular configurations, the intermediate, third fibrous stratum 56 can have a relatively higher density than the associated first and second fibrous strata, as determined under restraining pressure of 1.38 KPa (0.2 psi). Additionally, the third fibrous stratum can include a distinctive change in the concentration or density of the fibrous material wherein the concentration or density of the third fibrous stratum decreases in a substantially non-stepwise configuration when moving towards the first fibrous stratum 52. The concentration or density of the third fibrous stratum can also decrease in a substantially non-stepwise configuration when moving towards the second fibrous stratum 54. In further aspects, the concentration or density change provided to the stabilized absorbent body by the third fibrous stratum can be characterized by a distinctive, concentration slope-value. To provide distinctive combinations of improved lateral wicking and improved distribution through the thickness of the stabilized absorbent body, the slope-value can be at least a minimum of about 2.6. The slope-value can alternatively be at least about 2.8, and optionally, can be at least about 3 to provide improved benefits. In other aspects, the slope-value can be not more than a maximum of about 5. The slope-value can alternatively be not more than about 4.8, and optionally, can be not more than about 4.5 to provide improved performance.

In the various arrangements of the invention, the change in the concentration or density in the intermediate, third fibrous stratum 56 can be employed to determine the thickness of the third fibrous stratum. A suitable technique for determining the thickness and the change in concentration or density of the third fibrous stratum is described in the "Testing" section set forth below.

The intermediate, third fibrous stratum 56 can include a relatively greater amount of wet-strength agent, as compared to the first fibrous stratum 52. Additionally, the third fibrous stratum 56 can include a relatively greater amount of wet-strength agent, as compared to the second fibrous stratum 54. In a desired aspect, the third fibrous stratum 56 includes a relatively greatest amount of wet-strength agent, as compared to the first and second fibrous strata. A more particular aspect of the invention can include a configuration wherein either or both of the first and second fibrous strata 52 and 54 are substantially free of the wet-strength agent. Desirably, at least the first fibrous stratum is substantially free of the wet-strength agent. Yet another aspect of the invention can provide the intermediate fibrous stratum with an amount of wet-strength agent which is not more than about one weight percent, as determined with respect to the weight of the overall absorbent body. More particularly, the wet-strength agent can be distributed to provide a dry add-on amount which is not more than about 1 wt % of the overall, total weight of the constituent fibrous strata employed to form the absorbent body 32. The dry add-on amount of the wet-strength agent can alternatively be not more than about 0.8 wt %, and optionally, can be not more than about 0.5 wt % to provide improved performance. In other aspects, the dry add-on amount of the wet-strength agent can be at least a minimum of about 0.001 wt % of the total weight of the fibrous strata employed to form the absorbent body. The dry add-on amount of the wet-strength agent can alternatively be at least about 0.002 wt % to provide improved effectiveness.

If the amount of the wet-strength agent is too high, the absorbent body can exhibit excessive stiffness or brittleness. If the amount of the wet-strength agent is too low, the absorbent body can exhibit poor strength and poor integrity.

In particular aspects, the absorbent body 32, and particularly the fibrous strata of the absorbent body can provide a selected composite wet tensile strength. In desired configurations, the absorbent body can have a composite wet-strength which is at least a minimum of about 0.1 grams-force, per 1-gsm ($g/m^2$) of basis weight, per 1-inch (2.54 cm) of width. The wet-strength can alternatively be at least about 0.15 gm per $g/m^2$ per inch (2.54 cm), and optionally, can be at least about 0.2 gm per $g/m^2$ per inch (2.54 cm) to provide improved performance. In other aspects, the wet-strength can be not more than a maximum of about 20 gm per $g/m^2$ per inch (2.54 cm). The wet-strength can alternatively be not more than about 5 gm per $g/m^2$ per inch (2.54 cm), and optionally, can be not more than about 1 gm per $g/m^2$ per inch (2.54 cm) to provide improved effectiveness.

If the wet-strength is too low, the absorbent body 32 can be excessively susceptible to cracking and breaking during ordinary use. If the wet-strength is too large, the absorbent body can be excessively stiff. A suitable technique for determining the wet tensile strength is set forth below in the "Testing" section of the present disclosure.

More particular aspects of the invention can include first and/or second fibrous strata 52 and 54 which are substantially free of the wet-strength agent. In other aspects, the first and/or second fibrous strata can be substantially dispersible in an aqueous liquid. Where a stratum is substantially free of the wet-strength agent, and where a stratum remains substantially dispersible in an aqueous liquid, the selected stratum can advantageously remain soft and provide a more comfortable feeling to the wearer. Accordingly, where a substantial majority of the wet-strength agent is operatively concentrated in the intermediate stratum 56, the absorbent body can better exhibit the desired combinations of more rapid intake of liquid, better distribution and transport of the liquid, greater softness, and higher wet-strength.

In desired aspects, the absorbent body 32 can include a configuration wherein at least a minimum of about 5 wt % of the absorbent body remains substantially dispersible in an aqueous liquid. Alternatively, at least about 20 wt %, and optionally, at least about 50 wt % of the absorbent body remains substantially dispersible in the aqueous liquid to provide improved performance. In other aspects, not more than a maximum of about 98 wt % of the absorbent body remains substantially dispersible in the aqueous liquid. Alternatively, not more than about 95 wt %, and optionally, not more than about 90 wt % of the absorbent body remains substantially dispersible in the aqueous liquid to provide improved effectiveness. A suitable technique for determining the percentage of the total absorbent body that remains substantially dispersible in an aqueous liquid is set forth below in the "Testing" section of the present disclosure.

The percentage of dispersibility is an indicator of the proper distribution of the wet-strength agent along the thickness (z) dimension of the absorbent body. If the amount of dispersibility is too low, the absorbent body can exhibit inadequate surface softness, and can exhibit an insufficient uptake rate of absorbed liquid into the absorbent body. If the amount of dispersibility is too high, the absorbent body can exhibit inadequate wet-strength and insufficient spreading of the absorbed liquid along the length and width (x-y) dimensions of the absorbent body.

Additional aspects of the invention can configure the absorbent body and the intermediate, third fibrous stratum 56 with a structure that provides a selected, remainder basis weight of substantially non-dispersible fibrous material. In particular configurations, the substantially non-dispersible, remainder basis weight of the absorbent body can be at least about 30 $g/m^2$. The remainder basis weight can alternatively be at least about 100 $g/m^2$, and optionally, can be at least about 150 $g/m^2$ to provided improved performance. A suitable technique for determining the substantially non-dispersible, remainder basis weight of a web is set forth below in the "Testing" section of the present disclosure.

The remainder basis weight is another indicator of the proper distribution of the wet-strength agent along the thickness (z) dimension of the absorbent body. If the remainder basis weight is too high, the absorbent body can exhibit inadequate surface softness, and can exhibit an insufficient uptake rate of absorbed liquid into the absorbent body. If the remainder basis weight is too low, the absorbent body can exhibit inadequate wet-strength and insufficient spreading of the absorbed liquid along the length and width (x-y) dimensions of the absorbent body.

In other aspects, the absorbent body 32 can have a desired combination of softness and wet-strength. Accordingly, the absorbent body can have a relatively bulky, overall composite thickness to provide desired cushioning and softness. Desirably, the composite thickness can be within the range of about 0.1–2.4 cm, as determined under a restraining pressure of 1.38 KPa (0.2 psi). The composite thickness of the absorbent body can alternatively be within the range of about 0.15–1 cm, and optionally can be within the range of about 0.2–0.8 cm to provide improved benefits.

In further aspects, the quantities of absorbent fibers in one or more of the fibrous strata of the absorbent body 32 can include hydrophilic fibers. Desirably, each of the first, second and third quantities of absorbent fibers can include hydrophilic fibers. The fibers may be naturally hydrophilic, or may be treated to render them hydrophilic. Such hydrophilic fibers can, for example, include softwood kraft pulp fibers, eucalyptus pulp fibers, rayon fibers, surface-modified synthetic fibers or other synthetic fibers, and the like, as well as combinations thereof.

In more particular arrangements, the quantity of absorbent fibers in one or more of the fibrous strata of the absorbent body 32 can include cellulosic fibers, such as cotton or wood pulp fibers. In desired arrangements, each of the first, second and third quantities of absorbent fibers can include cellulosic fibers.

The wet-strength agent can be of a polymeric or non-polymeric binder material that is capable of forming hydrogen bonds, ionic bonds or covalent bonds with the fiber. Accordingly, the appropriate liquid binder can be fiber-specific, and different fibers may require a different liquid binder to provide the desired performance. In desired configurations, the binder material can be a water-based solution. For cellulose fibers, suitable binders are well known for those skilled in the art.

Examples of suitable polymeric binders can include polypropylene glycol (PPG); polyethylene glycol (PEG); polyacrylic acid (PAA); poly(caprolactone) diol; polyamide; cationic acrylamide copolymers; polyamine; polyamide-polyamine-epichlorohydrin (KYMENE); cationic amine-epichlorohydrin wet-strength agents; polyethylene imine agents; polyamide-epichlorohydrin agents with cellulose ethers or cationic starches for improving paper wet-strength; polyacrylamides-glyoxal (e.g. PAREZ); urea-formaldehyde agents (UF); cationic modified ureaformalin agents; melamine-formaldehyde agents(MF); cationic modified melamine-formalin agents; polyethyleneimine (PEI); dialdehyde starch (DAS); proteinaceous adhesives treated with formaldehyde; cellulose xanthate (viscose); synthetic latexes; vegetable gums such as guar and bean gum; neutral (or alkaline-curing) thermosetting wet-strength agents; water-soluble polymers containing carboxyl groups or carboxylate ions as their alkali metal or ammonium salts; substantially non-thermosetting tertiary-amino polyamide-epichlorohydrin agents.

Some commercial liquid binders are KYMENE 557LX, a polyamidoamine modified with epichlorohydrin (Hercules); CREPEPLUS 75, 97, a polyamidoamine modified with low epichlorohydrin content (Betz Paper Chemicals); CREPETROL 190, a polyamidoamine modified with low epichlorohydrin content (Hercules); PEI, polyethylenimine, molecular weight 50,000–60,000, 50% (wt) an aqueous liquid (Aldrich Chemical Co.); PEI-E a polyethylenimine modified with epichlorohydrin, base polymer mol. wt. 20,000, 17% (wt) an aqueous liquid (Aldrich Chemical Co.); POLYMIN PR971L, a high charge density, high molecular weight polyethylenimine (BASF); POLYMIN SNA, a modified high molecular weight polyethylenimine (BASF); and AGEFLOC WT-20VHV, a poly(dimethyldiallylammonium chloride) (CPS Chemical).

Examples of non-polymeric binders can include glycerin; ascorbic acid; urea; glycine; pentaerythritol; a monosaccharide or a disaccharide; citric acid; glyoxal; tartaric acid; dipropylene glycol; and urea derivatives such as DMDHEU (dimethyldihydroxyethylurea). Suitable saccharides can include glucose, sucrose, lactose, ribose, fructose, mannose, arabinose, and erythrose.

In desired configuration, the wet-strength agent can include a poly(aminoamide)-epichlorohydrin material, such as KYMENE agent, which is available from Hercules Inc., a business having offices located in Wilmington, Del. In other desired configurations, the wet-strength agent can include a glyoxalated polyacrylamide material, such as PAREZ agent, which is available from Cytec Industries, a business having offices located in West Paterson, N.J.

In desired arrangements, the first fibrous stratum 52 has been airlaid, and substantially dry-formed. In other arrangements, the second fibrous stratum 54 has been airlaid and substantially dry-formed, and in further arrangements, the third fibrous stratum 56 has been dry-formed. In still other arrangements, the wet-strength agent has been distributed onto the fibers of the third fibrous stratum 56 during an air-laying of the third fibrous stratum. A liquid or liquefied form of the wet-strength agent is desirably employed during the distribution process. For example, the liquid, wet-strength agent can be liquefied or otherwise placed into its liquid condition by a melting of the agent, a dissolving of the agent in an operative liquid to provide a solution, a providing of a suspension or emulsion of the agent in an operative liquid, or the like, as well as combinations thereof. In desired configurations, the wet-strength agent has been distributed in a liquid solution form onto the fibers of the third fibrous stratum. In other aspects, the wet-strength agent has been distributed in an aqueous liquid form onto the fibers of the fibrous stratum.

Various techniques, such as spraying, may be employed to distribute the wet-strength agent into the third fibrous stratum 56, suitable spraying techniques can include hydraulic spray systems, air atomizing spray systems, ultra-sonic spray systems and the like; or printing techniques, such as ink jet printing and the like; as well as combinations thereof.

In particular aspects, the liquid state of the wet-strength agent is capable of wetting the fibrous material of at least the third fibrous stratum. Accordingly, the wet-strength agent can become spread out over a larger number area of the individual fibers, and over a larger number of the fibers to increase the effectiveness and efficiency of the low add-on amount of the wet-strength agent material.

The absorbent body may be substantially free of superabsorbent material. In desired configurations, the absorbent body 32 can include a selected quantity of superabsorbent material distributed therein.

In particular aspects, the quantity of superabsorbent material can be at least a minimum of about 1 wt % of the absorbent body 32. The quantity of superabsorbent material can alternatively be at least about 5 wt %, and optionally, can be at least about 10 wt % of the absorbent body to provide improved performance. In other aspects, the quantity of superabsorbent material can be not more than a maximum of about 80 wt % of the absorbent body 32. The quantity of superabsorbent material can alternatively be not more than about 60 wt %, and optionally, can be not more than about 40 wt % of the absorbent body to provide improved effectiveness.

In further configurations, the absorbent body 32, and particularly the fibrous strata of the absorbent body, can have a selected density. More particularly, the absorbent body can have a composite density which is can be at least a minimum of about 0.05 grams per cubic centimeter (g/cm$^3$). The composite density can alternatively be at least about 0.08 g/cm$^3$, and optionally, can be at least about 0.1 g/cm$^3$ to provide improved performance. In other aspects, the composite density can be not more than a maximum of about 0.4 g/cm$^3$. The composite density can alternatively be not more than about 0.3 g/cm$^3$, and optionally, can be not more than about 0.25 g/cm$^3$ to provide improved effectiveness. For the purposes of the present disclosure, the density is determined at a restraining pressure of 1.38 KPa (0.2 psi).

If the density is too high, the absorbent body can be excessively stiff and may exhibit excessive cracking. If the density is too low, the absorbent body can be excessively bulky or may exhibit excessive collapsing when wet.

In desired aspects, the third fibrous stratum 56 is a non-tissue portion. Accordingly, the third fibrous stratum does not provide a distinct tissue layer. Accordingly, the interface between the third fibrous stratum 56 and the first fibrous stratum 52 is substantially indistinct, and non-discrete. Similarly, the interface between the third fibrous stratum 56 and the second fibrous stratum 54 is substantially indistinct and non-discrete. Where a tissue provides a layer having a relatively uniform thickness, the agent-stabilized third fibrous stratum has, along the z-direction, a thickness 18 that is significantly irregular when observed at when moving along the lateral direction 24 and/or longitudinal direction 26.

The third fibrous stratum 56 can have a selected cross-directional width along the appointed transverse direction 24 of the absorbent body 32. In particular aspects, the cross-directional width of the intermediate, third fibrous stratum can be at least a minimum of about 5% of a cross-directional width of the absorbent body. The cross-directional width can alternatively be at least about 10%, and optionally, can be at least about 30% of the cross-directional width of the absorbent body to provide improved performance. In other aspects, the cross-directional width of the third fibrous stratum can be not more than a maximum of about 100% of the cross-directional width of the absorbent body 32. The cross-directional width can alternatively be not more than about 90%, and optionally, can be not more than about 80% of the cross-directional width of the absorbent body to provide improved effectiveness.

In more particular arrangements, the agent-containing, third fibrous stratum 56 can have a cross-directional width which is not more than about 90% of a cross-directional width of the first fibrous stratum 52. The width of the third fibrous stratum can alternatively be not more than about 80%, and optionally can be not more than about 70% of the cross-directional width of the first fibrous stratum.

In other particular arrangements, the agent-containing third fibrous stratum 56 can have a cross-directional width which is not more than about 90% of a cross-directional width of the second fibrous stratum 54. The width of the third fibrous stratum can alternatively be not more than about 80%, and optionally can be not more than about 70% of the cross-directional width of the second fibrous stratum 54.

In particular configurations, the current invention can provide improved absorption of blood and menses. For example, the third fibrous stratum 56 can be narrower than both the first and the second fibrous stratus, and can have a relatively higher density. The higher density of the third stratum can advantageously provide better liquid absorption and distribution relative to the first and second strata. As a result, the blood/menses can be preferentially absorbed in the third fibrous stratum 56. The advantages can include the following: (1) the liquid can be localized in the center (along the pad length) of the absorbent, reducing the probability of leakage; and (2) the liquid can be hidden between the first and second strata, making the product aesthetically more pleasant.

In particular aspects, the absorbent body 32 can exhibit an improved ability to intake and distribute absorbed liquids. In desired configurations, the absorbent body 32 can have a liquid wicking or distribution value that is at least a minimum of about 0.001 grams per minute, per 1-g/m$^2$ (gsm) of basis weight, per inch (2.54 cm) of sample width (g/(min*gsm*inch)). The distribution value can alternatively be at least about 0.0015 g/(min*gsm*inch) to provide improved performance. In other aspects, the distribution value can be up to about 0.005 g/(min*gsm*inch) or more. The distribution value can alternatively be up to about 0.004 g/(min*gsm*inch), and optionally, can be up to about 0.003 g/(min*gsm*inch) to provide improved effectiveness.

The distribution value is desirably as high as possible to provide increased spreading of the absorbed liquid and a more efficient utilization of the entire absorbent composite. If the distribution value is too low, there can be an inadequate spreading of the absorbed liquid and a less efficient use of the entire absorbent capacity of the absorbent material. In particular, the absorbent capacity of the material at the distal ends of the absorbent body may be underutilized. A suitable technique for determining the liquid distribution or wicking value is set forth below in the "Testing" section of the present disclosure.

The presence of a fibrous stratum which is substantially non-dispersible in an aqueous liquid can advantageously increase the wet-strength of the absorbent structure, and in particular aspects, the wet-strength can be provided while also maintaining desired levels softness, resiliency, flexibility, absorbency rate and absorbent capacity. A suitable technique for determining the non-dispersibility of an absorbent layer or stratum is set forth below in the "Testing" section of the present disclosure.

Testing

Wet (or Dry) Tensile Strength Test:

A suitable technique for determining the wet tensile strength of an absorbent body can employ the following equipment and procedure.

A tensile tester, such as a SINTECH Model 1/G tensile tester available from MTS Systems Corporation, a business having offices in Research Triangle Park, N.C. (or an equivalent device) is set to have a gage length of 1 inch (2.54 cm). The gage length is the distance from the upper edge of the lower jaw and the bottom edge of the upper jaw. The jaws should hold the sample without slipping, and should not cause a preferential rupture of the sample at the clamping edges of the jaws. The crosshead speed (speed at which the jaws move apart relative to each other) is set to 10 cm/min. The test sample is configured with a 2 inch (5.08 cm) width and a 3 inch (7.62 cm) Length. The sample is weighed to the nearest 0.01 g to later calculate basis weight. The basis weight of the sample (expressed as grams per square meter) is determined in a conventional manner by dividing the sample weight (in grams) by the area covered by the sample (e.g. the product of the length and the width (both in meters)). The sample is soaked in a 2% by weight $CaCl_2$ solution for 20 minutes (this soaking step is omitted when determining the dry tensile strength of a sample). After the sample is removed from the $CaCl_2$ solution, any tissue attached to the outside of the sample is removed from both sides of the sample. The weight of any such tissue removed should be subtracted from the weight of the sample measured above prior to computation of the sample basis weight. The sample is secured in the upper jaw of the tensile tester and then secured in the lower jaw of the tensile tester. The tensile tester is programmed (e.g. TESTWORKS for Windows Version 3.10, available from MTS Systems Corporation to measure the peak load in grams-force. The tensile strength value is normalized to account for the differences in basis weight.

Normalized Calculation:

$$\text{Wet or Dry tensile strength} = \frac{\text{Peak Load (grams - force)}}{\text{Basis Weight (g/m}^2\text{)} * \text{Sample Width (inch)}}$$

Figure 7:
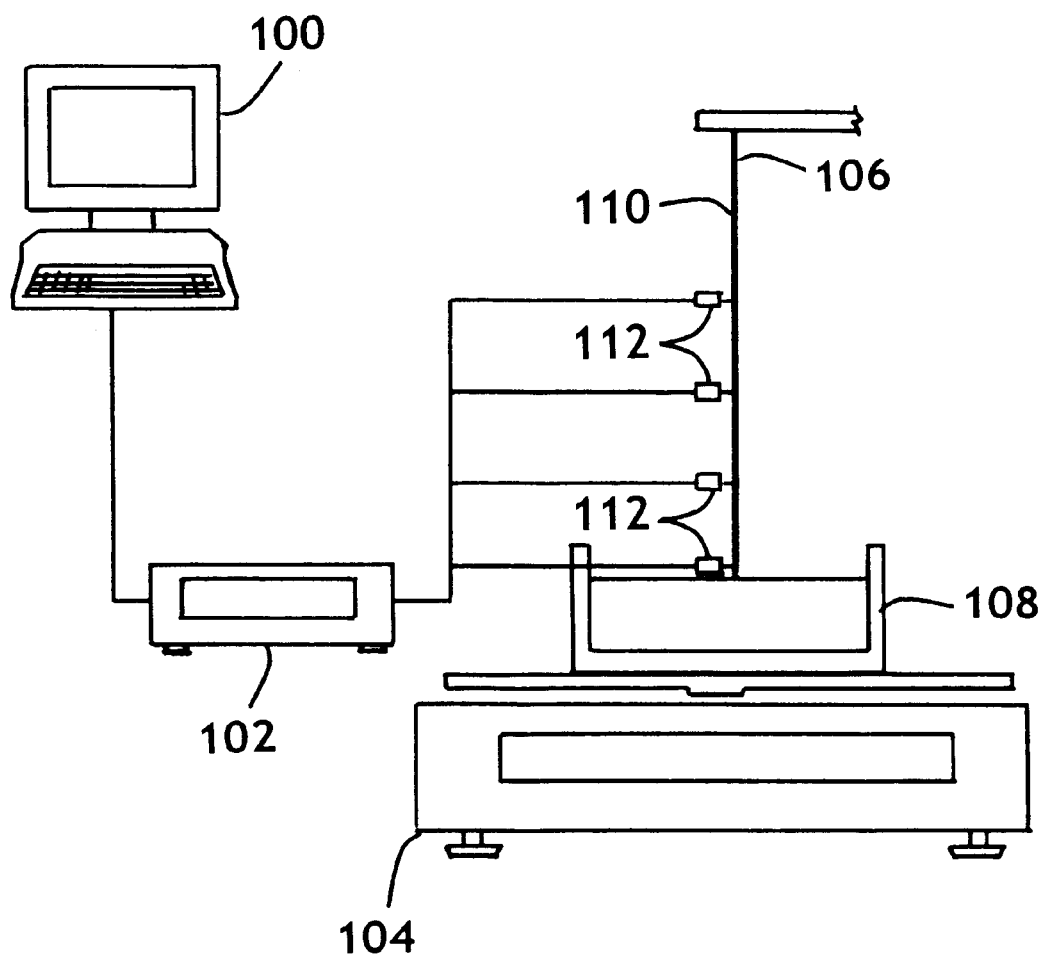
FIG. 7 representatively shows a schematic, side view of a system for determining vertical wicking flux values.

Level—Zero, Vertical Wicking, Liquid Distribution Test:

With reference to FIG. 7, a suitable technique for determining the wicking or liquid distribution value of an absorbent body that does not contain superabsorbent can employ the following equipment and procedures.

The test equipment includes a sample holder 106 which is composed of a rectangular frame that measures 5 inches (12.7 cm) wide and 12 inches (30.5 cm) long and has two matching halves. The frame includes appropriate, reinforcing cross members to ensure structural rigidity, and an example of a suitable material for constructing the frame is PLEXIGLAS polymer. Suitable alignment needles and holes are placed on the frames to match them up when they are brought together. A 4-mesh nylon screen is stretched and securely attached to each of the halves, and the two screens are appropriately constructed and arranged to sandwich and support the sample during the testing. The screens should preferably not apply any pressure and are present primarily to support the sample. Four sets of conventional liquid sensors are mounted on the frame, and each set includes two individual sensors. The purpose of these sensors is to indicate the presence of liquid, such as saline (water containing sodium chloride), at a particular location. For example, the sensors can be two pieces of conductive material that attached onto the opposite faces of the rectangular frame referenced above. Once the saline rises up in the sample to a particular height, an electrical connection and data signal would be established at the sensor at that particular location. The two sensors at each location are situated about 1 inch (2.54 cm) apart in the width direction of the frame. One set of sensors is positioned at each of four height elevations located at 0-cm, 5 cm, 10 cm and 15 cm height positions that are determined with respect to a selected end of the frame. The sensors are connected to a conventional computer 100 with a conventional electronic relay box 102, and are used to identify when the liquid has reached predetermined heights within the sample. Additionally, an electronic balance 104 is operatively connected to the computer, and the weighing system is configured to provide weight data approximately every second. A suitable balance is a model No. PM4800 which is capable of reading to 0.01 g and is available from Mettler Instrument Company, a business located in Hightstown, N.J. A substantially equivalent weighing device may also be employed. The balance is suitably arranged and configured to measure the weight of liquid that is lifted from the reservoir 108 by the vertically-upward wicking action of the test sample 110.

Each sample 110 is cut into a rectangle with a 2 inch (5.08 cm) width and a 10 inch (25.4 cm) length. The thickness under a pressure of 0.2 psi (1.38 KPa) and the weight of each sample are measured. The sample is placed on the nylon screen of one-half of the sample holder and aligned such that one end of the sample is coincident with the sensor at 0-cm, and the two sensors at each height are equal distances from their corresponding, more proximate side edge of the sample. Then, the other half of the frame is placed onto the first half and secured. The sample holder is now lowered vertically into a reservoir 108 that is sitting on the balance and contains 0.9% by weight of liquid saline. The sensor set at the 0-cm location is positioned towards the reservoir, and the dimensions and volume of the saline reservoir are chosen such that there will not be a substantial change in the level of saline through the course of the test. As soon as the sensor set at the 0-cm location indicates contact with saline, the downward motion of the sample is stopped, and the frame is held in position employing a suitable support. The weight of the saline reservoir is measured at one-second intervals using the computer 100. The sensors at the 5 cm, 10 cm and 15 cm height locations are employed to record the times taken for the saline to reach the respective heights. A detection data point for a sensor set is deemed to occur upon the first detection by either of the two sensors in the set. This test is run until liquid reaches the 15 cm height or sixty minutes have elapsed, whichever occurs sooner.

Calculations: The Liquid Pick Up Rate is computed from the data acquired from the balance. At each point in time, the Liquid Pick Up Rate may be obtained by taking the ratio of the differential amount of liquid picked up between adjacent data points and the time differential between those two data points. Alternately, a conventional data-smoothing technique, such as weighted moving average over a 5 second interval may be employed to smooth the time and balance data. Based on the sensor data, the time it took for the liquid to reach 15 cm is known. The Liquid Pick Up Rate at that time is denoted as the Liquid Pick Up Rate at 15 cm. The basis weight of the sample is computed by taking the weight of the sample in grams and dividing it by the area (0.0129 m$^2$) of a major surface of the sample. The Vertical Wicking Flux Value is then computed as follows:

$$(\text{Vertical Wicking Flux Value})_{15\text{ cm}} = \frac{\text{Liquid Pick Up Rate at 15 cm}}{\text{Basis Weight (g/m}^2\text{)} \times \text{Sample Width (inch)}}$$

If the liquid does not reach 15 cm within 60 minutes, the flux value is considered to be zero.

Vertical Wicking in SAM containing composites

A suitable technique for characterizing the wicking ability of composites containing superabsorbents is the following procedure.

Composite samples are cut to 9 inch (22.86 cm) length by 2.5 inch (6.35 cm) width. The weight and thickness of these samples are measured under a restraining pressure of 0.2 psi (1.38 KPa). The samples were suspended from a fixture that is capable of being lowered and raised. The reservoir of 0.9% w/w saline is placed on a balance. The sample is lowered into this reservoir and allowed to pick up 20 g of saline. The data from the balance is used to ascertain when 20 g has been picked up by the sample. An alternative, equivalent technique may optionally be used for this purpose. At this point the sample is raised out of the liquid and allowed to equilibrate for 30 minutes. At the end of the 30 minute waiting time, the sample is lowered into the saline reservoir again to pick up another 20 g of saline. Subsequently, it is raised and held outside the liquid reservoir for 30 minutes. The sample is then lowered for the third time into the liquid reservoir and allowed to pick up a final 20 g of saline. At the end of this step the sample is removed from the fixture and cut at the 10 cm mark from the end that was in the saline reservoir. The weight of the sample below the 10 cm mark and above the 10 cm mark are noted. The amount of saline present in the 2 sections of the sample may then be determined by drying the samples in an oven or any other suitable method. The ratio of the amount of saline above 10 cm height to the total amount of liquid in the composite is expressed as percentage of liquid above 10 cm.

Slope-Value Determination:

A suitable technique for determining the slope-value arising from the concentration or density changes of the material in an absorbent body can employ the following equipment and procedures. The technique may also be employed to determine the thickness of an intermediate, third fibrous stratum of an absorbent body.

Samples, which measure approximately 45-mm×27-mm, are cut from the submitted material with a single-edge razor blade. Typically the material has a "machine-direction", which is a dimension of the material which substantially corresponds to the direction along which the material was moving during the process employed to make the material. These samples are vacuum impregnated with an epoxy material within a mold, and are compression embedded at a pre-determined pressure. Thin-section specimens are then cut and prepared for image analysis. A suitable epoxy material is Struers EPOFIX epoxy which is available from Electron Microscopy Sciences Company, a business having offices located in Fort Washington, Pa.; or an equivalent material. A suitable embedding mold is the 46-mm×28-mm× 20-mm polypropylene PEEL-A-WAY mold, or an equivalent. These embedding molds are available from Electron Microscopy Sciences Company. A suitable vacuum impregnator system is a BUEHLER Model 20-1384-115 vacuum impregnator which is available from Buehler, Ltd., a business having offices located in Lake Bluff, Ill.; or an equivalent system.

Figure 8:
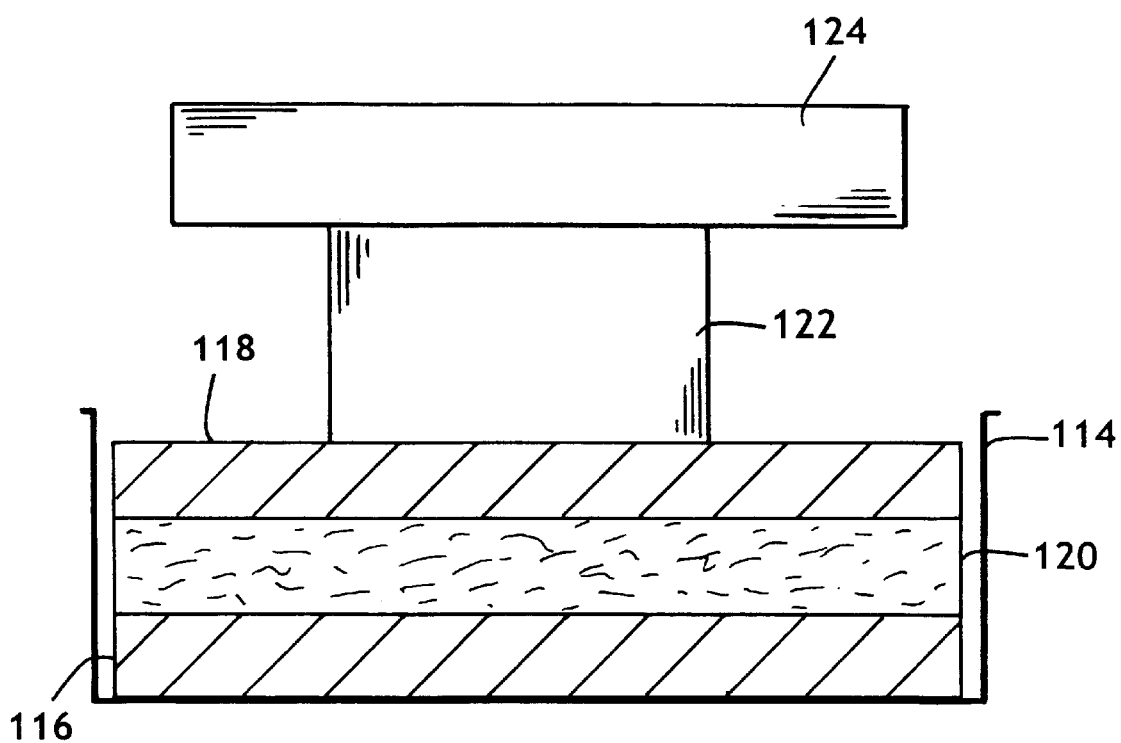
FIG. 8 representatively shows a schematic, side view of a system for compression embedding a sample for preparing specimens for image analysis.

For the compression embedding operation, a selected sample 120 is assembled within an embedding mold 114 between two pre-hardened plates composed of EPOFIX epoxy, as representatively shown in FIG. 8. These pre-hardened epoxy plates measure 46-mm×28-mm with a thickness of 3-mm, and can be formed by hardening appropriate measures of the EPOFIX epoxy in the embedding molds described above. The purpose of the epoxy plates is to uniformly distribute the applied pressure. A pre-hardened epoxy base plate 116 is placed in the bottom of the embedding mold 114, the sample 120 is placed on this base, and the sample is covered with a pre-hardened epoxy cover platel 18.

This sandwich assembly is vacuum impregnated with epoxy as follows. A measured weight of liquid epoxy resin is out-gassed in the impregnator at −30 inches Hg for about 10 minutes. Any surface bubbles that form can be disrupted by brief pressure excursions which cycle the pressure to −10 inches Hg and then back to −30 inches Hg. The pressure cycles are repeated as needed to sufficiently remove the bubbles. After removing the resin from the impregnator, an appropriate weight of catalyst is added and mixed. The embedding mold containing the sample assembly is placed in the impregnator, along with the mixed epoxy resin, and the impregnator is evacuated to −30 inches Hg. The pressure is again cycled between −10 inches Hg and −30 inches Hg for about ten minutes, or until the epoxy reaches an out-gas equilibrium. The liquid epoxy resin is then poured into the embedding mold at a vacuum of −26 inches Hg. Once the sample assembly is covered with the epoxy resin, the impregnator is immediately brought back to ordinary atmospheric pressure.

The vacuum-impregnated samples are hardened in the epoxy under a restraining pressure of 0.55 psi (3.79 KPa), employing the arrangement representatively shown in FIG. 8. A polypropylene spacer cup 122 is placed on top of the vacuum impregnated sample assembly that is composed of the sample 120, the pre-hardened epoxy plates 116 and 118 that sandwich the sample, and the liquid epoxy resin. An appropriate amount of weight 124 is then placed on top of the polypropylene cup. The polypropylene cup is used to prevent embedding the weight in the epoxy, which would hinder standard sectioning methods. The amount of weight used will depend on the area of the pre-hardened epoxy cover, and can be selected by employing the following formula:

$$psi = \frac{\text{weight (pounds)}}{\text{area of cover (sq. in.)}}; \quad \text{Example: } 0.55\ psi = \frac{1.11\ \text{pounds}}{1.99\ \text{inch}^2}$$

The pre-hardened epoxy base and cover are intended to be neutrally buoyant and not contribute to the weight of compression.

The thin-section specimens for image analysis are cut parallel to the "machine-direction" of the sample material. Additional thin-sections may be cut perpendicular to the "machine-direction" to check for uniformity in the various strata, particularly in the third fibrous stratum. The uniformity is, however, not required for the present invention. Three or more millimeters are trimmed from the end of sample block before the thin-sections are collected. Two 20-$\mu$m scrap sections are cut just prior to collecting the two, 40-$\mu$m sections, which are sliced at a cutting speed of 4-mm/sec. A suitable sectioning device is a Model POLY-CUT E SLEDGE microtome which is available from Reichert-Jung, a business having offices located in Heidelberger Strasse, West Germany; or an equivalent device. The thin-section specimens are mounted to glass slides with a suitable bonding material, such as the Struers EPOFIX epoxy, or an equivalent material.

Three, thin-section specimens are sliced from each sample material employing conventional sectioning techniques and equipment. After the preparation of the thin-section specimens, the analysis is conducted on the specimens, as follows.

The testing employs an image analysis system that is coupled with a microscope and an auto-staging device. Additionally, the testing employs a low-magnification condenser with transmitted bright-field illumination. A suitable image analysis system is a Leica/Cambridge QUANTIMET 970 Image Analysis System (available from Leica Corp., a business having offices in Deerfield, Ill.), or an equivalent system. A suitable microscope is an OLYMPUS BH-2 microscope (available through Leica Corp.) fitted with a 4×objective, or an equivalent combination of components. A suitable auto-staging device is a MERZHAUSER 4×8-inch autostage (available through Leica Corp), or an equivalent device.

The image analysis system is programmed to run with the following routine, designated as "SLOPE". The operation and terminology of the routine is well known to those skilled in the art of image analysis.

Cambridge Instruments QUANTIMET 970
QUIPS/MX: V08.00
USER:
ROUTINE: SLOPE
DATE:
RUN:
SPECIMEN:
Enter specimen identity
Scanner (No. 2 Chalnicon    LV = 5.06 SENS = 1.46 PAUSE)
SUBRTN STANDARD
Load Shading Corrector       (pattern - STD)
Calibrate User Specified    (Cal Value = 3.810 microns per pixel)
PERCAREA = 0.

-continued

```
TOTPERCAR = 0.
STAGEX = 100000.
STAGEY = 25000.
Stage Move      (STAGEX, STAGEY)
Stage Scan    (           X          Y
              scan origin  STAGE X   STAGE Y
              field size   800.0     38.0
              no. of fields  1       180 )
Detect 2D     (Darker than 48. Delin PAUSE)
For FIELD
Scanner       (No. 2 Chalnicon
              AUTO-BRIGHTNESS SENS = 1.46)
Live Frame is Rectangle (X: 280,  Y: 347,  W: 255,  H: 6.)
Detect 2D     (Darker than 48, Delin)
Measure field - Parameters into array FIELD
PERCAREA = 100. * FIELD AREAFRACT
Distribute PERCAREA (Units %) vs FIELDNUM (Units #)
  into GRAPH from 0.00 to 180.00 into 60 bins. differential
Stage Step
Next FIELD
Print FIELD
Print Distribution (GRAPH. differential, bar chart, scale = 250.00
For LOOPCOUNT = 1 to 10
Print LOOPCOUNT
Next
Print Distribution  (GRAPH, - cumulative, bar chart, scale = 0.00)
END OF PROGRAM
```

Using the image analysis system the operator can observe the presence of a layer region having a relatively higher concentration of material. The high-concentration region is typically evidenced by a visibly higher, area-density of observed, "dark" material within the high-concentration region. For example, the high-concentration region can be provided by a third stratum which provides a desired "lateral wicking region" or "stabilized layer region" in an absorbent sample that incorporates the present invention. The presence of the stabilized, third stratum region can be evidenced by a distinctive distribution of the higher concentration of the "dark" material observed in the "stabilized layer region". As the operator observes the auto-stage move the specimen or otherwise index the small line-frame to "enter" into and "exit" from the "stabilized layer region", the operator notes the field numbers that correspond to those "enter" and "exit" locations. The distance between the "enter" and "exit" locations along the z-directional thickness of the sample is the thickness of the stabilized intermediate layer. The stage indexing and the image analysis system generate individual scans across the specimen being analyzed. For each scan, the stage indexing and the image analysis system can produce a cumulative percent-area (% A) histogram, an example of which is representatively shown in FIG. 9A.

In a histogram of an absorbent body having the stabilized, intermediate stratum of the invention, the "entry" and "exit" fields are further evidenced by the three regions and the two distinctive transitions found in the cumulative % A histogram that are caused by the presence of the stabilized, lateral wicking region. As representatively shown in FIG. 9C, the plot in each of the three regions can determine an individual line, and the two intersection points of the three lines can be used to help determine the "entry" and "exit" fields. This technique may also be employed to determine the z-directional thickness of the intermediate, third fibrous stratum.

After the cumulative % A histogram is printed for each scan (or is otherwise displayed or presented in an electronic or non-electronic format suitable for further analysis), the operator extracts the field counts (now called "classes") and the cumulative % A values from that histogram.

The operator plots the cumulative % A versus the class-difference for each scan. The plot begins at the location of the "entry" field of the transition region, and ends at the location of the "exit" field of the transition region, as representatively shown in FIG. 9B. The plotted values are used to determine a best fit line, and the slope of this line is the slope-value provided by the third fibrous stratum of the particular scan.

Three specimens (thin-section slices) for each sample, and two scans are conducted per specimen. The locations of the two scans are spaced sufficiently far apart to effectively provide data sets that substantially independent from each other. The six scans provide six data sets, and to determine the final "slope-value" of an absorbent sample, the six data sets are employed to generate six individual plots which are employed to determine six individual, preliminary slope-values. The six preliminary slope-values are then arithmetically averaged to determine the final slope-value of the sample.

Saline Separation Test:

A suitable technique for determining the presence of a substantially non-dispersible stratum, and the basis weights of non-dispersible and/or dispersible strata can employ the following equipment and procedures.

The absorbent sample to be tested is die-cut to 2.25 inch (5.715 cm) diameter circular disk. The forming tissue, if any, is removed from the dry sample and the sample is weighed to the nearest 0.01 g to determine the initial weight of the dry absorbent sample. Approximately 400 ml of 0.9% w/w saline solution are placed in an operative container, such as a 800 ml PYREX beaker. A 1.5 inch (3.81 cm) magnetic stir bar is placed in the bottom of the 800 ml PYREX beaker, and the beaker is placed on a magnetic stir plate, such as a Model No. 04644 (available from Cole Parmer Instrument Company, a business having offices located in Vernon Hills, Ill.), or an equivalent device. The magnetic stir plate is set to 200 rpm. The absorbent sample is placed in the beaker of saline, and allowed to stir for 3 minutes. After 3 minutes, the stabilized layer (the remaining portion of absorbent that is still intact) is removed from the beaker, and is weighed to the nearest 0.01 g. The stabilized layer material is placed in an oven to dry for 30 minutes (or until completely dry) at 100 degrees Celsius. The material of the dry, stabilized layer is weighed to the nearest 0.01 g.

Calculations:

Weight of Removed Portion (g)=Initial weight of the dry absorbent sample(g), minus the weight of the remaining portion of the dry stabilized layer material (g)

Basic Weight of Dispersible Portion =
$$\frac{\text{Weight of Removed Portion (grams)}}{\text{Area of Sample (m}^2\text{)}}$$

Basic Weight of Non-Dispersible Portion =
$$\frac{\text{Weight of Remaining Portion (grams)}}{\text{Area of Sample (m}^2\text{)}}$$

$$\% \text{ Stabilized} = \frac{\text{Weight of remaining dry stabilized layer material}}{\text{Initial weight of total dry absorbent sample}}$$

The following examples are given to provide a more detailed understanding of the invention. The particular materials, dimensions, amounts and other parameters are exemplary, and are not intended to specifically limit the scope of the invention. In the examples, the absorbent body samples for each of the codes had the compositions and structures summarized in following Table A. Information regarding the viscosities of the wet-strength agents employed in the various samples are summarized in the following Table B.

TABLE A

Compositions

| Sample Number | WSA type | SAM % | WSA distri-bution | WSA add-on % | WSA add-on g/m² | water add-on g/m² | #sheets/ sheet BW g/m² | density g/cm³ | cure Temp-° C.; Time-min |
|---|---|---|---|---|---|---|---|---|---|
| 1 | KYM 557 | 0 | L | 0.1 | 0.4 | 40 | 2/200 | 0.15 | 100; 30 |
| 2 | KYM 557 | 0 | L | 0.3 | 1.2 | 39 | 2/200 | 0.15 | 100; 30 |
| 3 | KYM 557 | 0 | L | 0.5 | 2 | 38 | 2/200 | 0.15 | 100; 30 |
| 4 | KYM 557 | 0 | L | 1 | 4 | 36 | 2/200 | 0.15 | 100; 30 |
| 5 | KYM 557 | 0 | U | 0.1 | 0.4 | 40 | 8/50 | 0.15 | 100; 30 |
| 6 | KYM 557 | 0 | U | 0.3 | 1.2 | 39 | 8/50 | 0.15 | 100; 30 |
| 7 | KYM 557 | 0 | U | 0.5 | 2 | 38 | 8/50 | 0.15 | 100; 30 |
| 8 | KYM 557 | 0 | U | 1 | 4 | 36 | 8/50 | 0.15 | 100; 30 |
| 9 | none | 0 | none | 0 | 0 | 0 | 2/200 | 0.15 | |
| 10 | none | 0 | none | 0 | 0 | 40 | 2/200 | 0.15 | |
| 11 | none | 0 | none | 0 | 0 | 36 | 8/50 | 0.15 | |
| 12 | KYM 450 | 0 | L | 0.1 | 0.4 | 40 | 2/200 | 0.15 | 100; 30 |
| 13 | KYM 450 | 0 | L | 0.5 | 2 | 39 | 2/200 | 0.15 | 100; 30 |
| 14 | KYM 450 | 0 | U | 0.1 | 0.4 | 38 | 8/50 | 0.15 | 100; 30 |
| 15 | KYM 450 | 0 | U | 0.5 | 2 | 36 | 8/50 | 0.15 | 100; 30 |
| 16 | PAR 631 | 0 | L | 0.1 | 0.4 | 40 | 2/200 | 0.15 | 100; 30 |
| 17 | PAR 631 | 0 | L | 0.5 | 2 | 39 | 2/200 | 0.15 | 100; 30 |
| 18 | PAR 631 | 0 | U | 0.1 | 0.4 | 38 | 8/50 | 0.15 | 100; 30 |
| 19 | PAR 631 | 0 | U | 0.5 | 2 | 36 | 8/50 | 0.15 | 100; 30 |
| 20 | FLEXBD | 0 | L | 1 | 4 | 39 | 2/200 | 0.15 | air dry |
| 21 | FLEXBD | 0 | U | 1 | 4 | 35 | 8/50 | 0.15 | air dry |
| 22 | HM Adh | 0 | L | 1 | 4 | | 2/200 | 0.15 | air dry |
| 23 | HM Adh | 0 | L | 5 | 20 | | 2/200 | 0.15 | air dry |
| 24 | HM Adh | 0 | U | 1 | 4 | | 8/50 | 0.15 | air dry |
| 25 | HM Adh | 0 | U | 5 | 20 | | 8/50 | 0.15 | air dry |
| 26 | KYM 557 | 20 | L | 0.3 | 1.2 | 39 | 2/200 | 0.15 | 100; 30 |
| 27 | KYM 557 | 40 | L | 0.3 | 1.2 | 39 | 2/200 | 0.15 | 100; 30 |
| 28 | KYM 557 | 60 | L | 0.3 | 1.2 | 39 | 2/200 | 0.15 | 100; 30 |
| 29 | KYM 557 | 20 | L | 0 | 0 | 0 | 2/200 | 0.15 | 100; 30 |
| 30 | KYM 557 | 40 | L | 0 | 0 | 0 | 2/200 | 0.15 | 100; 30 |
| 31 | KYM 557 | 60 | L | 0 | 0 | 0 | 2/200 | 0.15 | 100; 30 |
| 32 | KYM 557 | 0 | L | 0.3 | 1.2 | 39 | 2/200 | 0.1 | 100; 30 |
| 33 | KYM 557 | 0 | L | 0.3 | 1.2 | 39 | 2/200 | 0.2 | 100; 30 |
| 34 | KYM 557 | 0 | L | 0.3 | 1.2 | 39 | 2/200 | 0.3 | 100; 30 |
| 35 | KYM 557 | 0 | L | 0.3 | 1.2 | 39 | 2/200 | 0.4 | 100; 30 |
| 36 | KYM 557 | 0 | L | 0.1 | 0.4 | 19.6 | 2/200 | 0.1 | 100; 30 |
| 37 | KYM 557 | 0 | L | 0.1 | 0.4 | 19.6 | 2/200 | 0.2 | 100; 30 |
| 38 | KYM 557 | 0 | L | 0.1 | 0.4 | 19.6 | 2/200 | 0.25 | 100; 30 |
| 39 | KYM 557 | 0 | L | 0.1 | 0.4 | 19.6 | 2/200 | 0.3 | 100; 30 |
| 40 | KYM 557 | 0 | L | 0.05 | 0.2 | 10 | 2/200 | 0.15 | 100; 30 |
| 41 | KYM 557 | 0 | L | 0.1 | 0.4 | 20 | 2/200 | 0.15 | 100; 30 |
| 42 | KYM 557 | 0 | L | 0.4 | 1.6 | 80 | 2/200 | 0.15 | 100; 30 |
| 43 | KYM 557 | 0 | L | 0.8 | 3.2 | 160 | 2/200 | 0.15 | 100; 30 |
| 44 | KYM 557 | 0 | L | 2.0 | 8 | 400 | 2/200 | 0.15 | 100; 30 |

TABLE B

Viscosities

| Sample Number | WSA type | Viscosity-Centipoise | Temperature-° C. |
|---|---|---|---|
| 1 | KYM 557 | 2.4 | 22 |
| 2 | KYM 557 | 4.5 | 22 |
| 3 | KYM 557 | 7.9 | 22 |
| 4 | KYM 557 | 18.3 | 22 |
| 5 | KYM 557 | 2.4 | 22 |
| 6 | KYM 557 | 4.5 | 22 |
| 7 | KYM 557 | 7.9 | 22 |
| 8 | KYM 557 | 18.3 | 22 |
| 12 | KYM 450 | 4.1 | 22 |
| 13 | KYM 450 | 12.0 | 22 |
| 14 | KYM 450 | 4.1 | 22 |
| 15 | KYM 450 | 12.0 | 22 |
| 16 | PAR 631 | 1.4 | 22 |
| 17 | PAR 631 | 5.3 | 22 |
| 18 | PAR 631 | 1.4 | 22 |
| 19 | PAR 631 | 5.3 | 22 |
| 20 | FLEXBD | 1.3 | 22 |
| 21 | FLEXBD | 1.3 | 22 |
| 22 | HM Adh | 6750 | 143 |
| 23 | HM Adh | 6750 | 143 |
| 24 | HM Adh | 6750 | 143 |
| 25 | HM Adh | 6750 | 143 |
| 26 | KYM 557 | 4.5 | 22 |
| 27 | KYM 557 | 4.5 | 22 |
| 28 | KYM 557 | 4.5 | 22 |
| 31 | KYM 557 | | |
| 32 | KYM 557 | 4.5 | 22 |
| 33 | KYM 557 | 4.5 | 22 |

TABLE B-continued

| | | Viscosities | |
|---|---|---|---|
| Sample Number | WSA type | Viscosity- Centipoise | Temperature- ° C. |
| 34 | KYM 557 | 4.5 | 22 |
| 35 | KYM 557 | 4.5 | 22 |

WSA = Wet-Strength Agent.
BW = Basis Weight.
FLEXBD = FLEXBOND material.
HM Adh = Hot Melt Adhesive.
KYM = KYMENE material.
PAR = PAREZ material.
SAM = Super Absorbent Material (FAVOR 880 superabsorbent).
sheets = Number of individual sheets of absorbent fluff material employed to assemble the overall, total absorbent composite.
L = Layered distribution of the wet-strength agent in the absorbent composite.
U = substantially Uniform distribution of the wet-strength agent within the absorbent composite.
WSA Add-on % was computed as a percentage of total basis weight of the absorbent composite.

Each final absorbent composite had a 400 g/m² basis weight of dry woodpulp fluff material, and CR1654 was the type of woodpulp fluff used.

| | |
|---|---|
| KYM 557 | pH = 7.5 |
| KYM 450 | pH = 8.0 |
| PAREZ | pH = 4.5 |

In the samples designated as "L", the absorbent body composite was composed of one or more sub-component sheets that are stacked and assembled together to provide the desired, total composite basis weight. The distribution of the wet-strength agent had a layered configuration within the absorbent body composite, and the added water or binder material was substantially restricted to the selected intermediate, third stratum or layer that was sandwiched between two other strata or layers of the absorbent composite.

In the samples designated as "U", the absorbent body composite was composed of one or more sub-component sheets that are stacked and assembled together to provide the desired, total composite basis weight. Each sheet has a substantially uniform distribution of the wet-strength agent, and the added water, binder or wet-strength agent is substantially evenly distributed through the thickness of the sheet. As a result, the added water, binder or wet-strength agent is substantially evenly distributed through the thickness of the absorbent composite.

The stabilized airformed materials were prepared in a handsheet former using COOSA CR1654 fluff, which is available from US Alliance Forest Products Corporation, a business having offices located in Coosa Pines, Ala. The basis weight of the total absorbent of each absorbent composite, not including the wet-strength agent and moisture, was 400 gsm (g/m²). Sub-component, fluff sheets of the selected basis weights were first formed and cut into handsheets of the desired size of 5 inch×15 inch (12.7 cm×38.1 cm).

A wet-strength agent solution was prepared by adding water to obtain the desired percent concentration. Sodium carbonate was added to the solution to obtain the appropriate pH for each type of wet-strength resin to improve the cross-linking efficiency of the solution (e.g. see the listing of appropriate pH provided after Table B). Optionally, sodium bicarbonate may be substituted.

Figure 6:
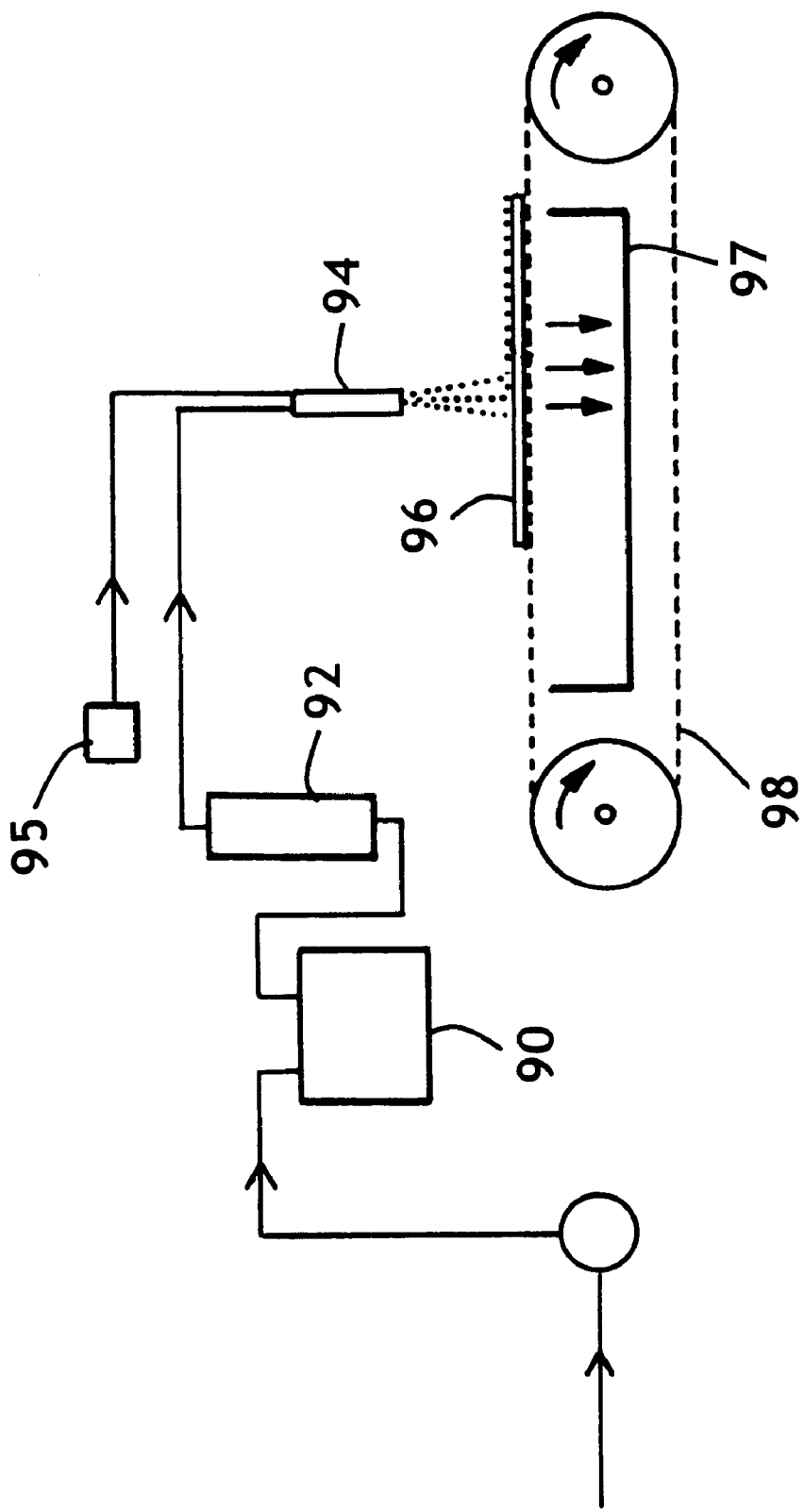
FIG. 6 representatively shows a schematic, side view of a system for distributing liquid wet-strength agent into component fluff sheets.

To prepare a sample having a substantially uniform distribution of wet-strength agent through the thickness of the sample, the prepared liquid agent was sprayed onto each of the desired number of low basis weight, sub-component fluff sheets using the equipment shown in FIG. 6. As representatively shown, a suitable air source delivers high-pressure air to operatively pressurize a reservoir tank 90 of the liquid wet-strength agent. The agent is deliver from the tank 90, through a flow meter 92 and into a spray nozzle 94. Another air supply 95 delivers process spraying air to the nozzle 94. The desired fluff sheet 96 is transported past the spray nozzle on a moving, foraminous surface provided by a conventional wire screen, endless belt system 98, and a conventional vacuum system 97 was configured to draw an operative air flow through the forming surface. Accordingly, the spraying system provided a method which consistently and uniformly sprayed the liquid wet-strength agent on the individual fluff sheets.

To prepare a sample having a layered, stratified distribution of wet-strength agent, the selected wet-strength agent was sprayed onto a first, sub-component fluff sheet. The sprayed fluff sheet was immediately plied together with another unsprayed, sub-component fluff sheet, and the fluff sheets were pressed together using a mechanical press.

The absorbent composites were pressed to the desired density by appropriately selecting the shim thicknesses employed with the press. All samples, with the exception of the samples that included hot melt adhesive or FLEXBOND binder, were cured in an oven at 100° C. for 30 minutes.

EXAMPLE 1

The properties of the absorbent bodies employed in this Example are summarized in the following Table 1.

TABLE 1

| | Wet absorbent tensile | |
|---|---|---|
| Sample | Code | g/gsm/inch (2.54 cm) |
| 9 | Control | 0.0798 |
| 10 | water - L | 0.0889 |
| 1 | 0.1% KYMENE 557-L | 0.3488 |
| 2 | 0.3% KYMENE 557-L | 0.3495 |
| 3 | 0.5% KYMENE 557-L | 1.0757 |
| 4 | 1.0% KYMENE 557-L | 1.7481 |
| 9 | Control | 0.0798 |
| 11 | water - U | 0.0966 |
| 5 | 0.1% KYMENE 557U | 0.1239 |
| 6 | 0.3% KYMENE 557U | 0.1305 |
| 7 | 0.5% KYMENE 557U | 0.2103 |
| 8 | 1.0% KYMENE 557U | 0.2112 |

With reference to the information provided by Table 1, the absorbent configurations which incorporate the present invention can exhibit an advantageous combination of high wet-strength and low amounts of the wet-strength agent. In particular, structures stabilized with KYMENE 557 have a higher wet tensile strength than structures stabilized with water-only. Additionally, the layered distribution of the wet-strength agent provides higher wet-strength, as compared to the uniform distribution of the wet-strength agent, and higher amounts of wet-strength agent provide to higher wet-tensile strengths.

EXAMPLE 2

The properties of the absorbent bodies of this Example are summarized in the following Table 2.

TABLE 2

Wet absorbent tensile

| Sample | Code | g/gsm/inch (2.54 cm) |
|---|---|---|
| 9 | Control | 0.0798 |
| 12 | 0.1% KYMENE 450 - L | 0.1973 |
| 13 | 0.5% KYMENE 450 - L | 0.4750 |
| 14 | 0.1% KYMENE 450 - U | 0.1040 |
| 15 | 0.5% KYMENE 450 - U | 0.1088 |

With reference to Table 2, it can be observed that an absorbent structure constructed with KYMENE 450 can also provide a higher wet-tensile strength when the wet-strength agent is arranged in a layered distribution, as compared to a uniform distribution. KYMENE 450 is an example of a wet-strength agent which has a low viscosity, as shown in Table B, and is an example of a wet-strength agent which has a poly(aminoamide)-epichlorohydrin based chemistry.

EXAMPLE 3

The properties of the absorbent structures of this Example are summarized in the following Table 3.

TABLE 3

Wet absorbent tensile

| Sample | Code | g/gsm/inch (2.54 cm) |
|---|---|---|
| 9 | Control | 0.0798 |
| 16 | 0.1% PAREZ 631 - L | 0.4358 |
| 17 | 0.5% PAREZ 631 - L | 1.3647 |
| 18 | 0.1% PAREZ 631 - U | 0.1209 |
| 19 | 0.5% PAREZ 631 - U | 0.2295 |

With reference to Table 3, it can be observed that an absorbent structure constructed with PAREZ 631 can also provide a higher wet-tensile strength when the wet-strength agent is arranged in a layered distribution, as compared to a uniform distribution. PAREZ 631 is an example of a wet-strength agent which has a low viscosity, as shown in Table B, and is an example of a wet-strength agent which has a glyoxylated polyacrylamide based chemistry.

EXAMPLE 4

The properties of the absorbent bodies of this Example are summarized in the following Table 4.

TABLE 4

Wet absorbent tensile

| Sample | Code | g/gsm/inch (2.54 cm) |
|---|---|---|
| 9 | Control | 0.0798 |
| 20 | 1.0% FLEXBOND - L | 0.096 |
| 21 | 1.0% FLEXBOND - U | 0.0962 |

With reference to Table 4, it can be observed that the FLEXBOND binder material provides lower levels of wet-strength, even at higher add-on amounts. The binder was a FLEXBOND 165 material available from Air Products & Chemicals, Inc., a business having offices in Allentown, Pa. The FLEXBOND binder is an example of a wet-strength agent which does not provide high wet-strength even at high add-on levels, and even though the binder has a relatively low viscosity (e.g. see Table B).

EXAMPLE 5

The properties of the absorbent bodies of this Example are summarized in the following Table 5.

TABLE 5

Wet absorbent tensile strength

| Sample | Code | g/gsm/inch (2.54 cm) |
|---|---|---|
| 9 | Control | 0.0798 |
| 22 | 1.0% Hot Melt Adhesive - L | 0.3067 |
| 23 | 5.0% Hot Melt Adhesive - L | 1.1944 |
| 24 | 1.0% Hot Melt Adhesive - U | 0.1147 |
| 25 | 5.0% Hot Melt Adhesive - U | 0.3442 |

With reference to Table 5, it can be observed that holt melt adhesive needs to be provided at significantly higher add-on levels to generate desired levels of wet-strength. The high viscosity (e.g. see Table B) of the hot melt adhesive reduces its ability to spread over the surface of the absorbent fibers, and reduces its ability to provide desired levels and distributions of wet-strength bonding.

EXAMPLE 6

The properties of the absorbent bodies of this Example are summarized in the following Table 6.

TABLE 6

Wet absorbent tensile strength (SAM concentration)

| Sample | Code | | g/gsm/inch (2.54 cm) |
|---|---|---|---|
| 26 | 0.3% KYMENE 557 | 20% SAM | 0.1146 |
| 27 | 0.3% KYMENE 557 | 40% SAM | 0.091 |
| 28 | 0.3% KYMENE 557 | 60% SAM | 0.055 |
| 29 | | 20% SAM | 0.0587 |
| 30 | | 40% SAM | 0 |
| 31 | | 60% SAM | 0 |

With reference to Table 6, it can be observed that the desired stabilization of the absorbent structure can be generated in composites that contain SAM (superabsorbent material). This is surprising, since it is ordinarily expected that the swelling of the superabsorbent material would break the bonds formed by the low amounts of wet-strength agent, and would reduce the wet-strength to the levels provided in composites where the wet-strength agent is absent.

EXAMPLE 7

The properties of the absorbent bodies of this Example are summarized in the following Table 7.

TABLE 7

Wet absorbent tensile strength (density effect)

| Sample | Code | g/gsm/inch (2.54 cm) |
|---|---|---|
| 32 | 0.3% KYMENE 557- 0.1 g/cc | 0.1696 |
| 33 | 0.3% KYMENE 557- 0.2 g/cc | 0.1483 |
| 34 | 0.3% KYMENE 557- 0.3 g/cc | 0.2289 |
| 35 | 0.3% KYMENE 557- 0.4 g/cc | 1.2075 |

With reference to Table 7, it can be observed that increasing the density of the absorbent structure can further increase the effectiveness of the stabilizing wet-strength agent in producing greater wet tensile strength. As the density is increased, more bonds can be formed during the curing process, and higher wet-tensile strengths can be produced.

EXAMPLE 8

A saline separation test was conducted on each sample employed in this Example, and the properties of the sample absorbent bodies are summarized in the following Table 8.

TABLE 8

Saline Separation test results

| Sample | Code | % stabilized |
|---|---|---|
| 9 | Control | 0 |
| 10 | water - L | 0 |
| 36 | 0.1% KYMENE 557 0.10 g/cc | 17.97 |
| 1 | 0.1% KYMENE 557 0.15 g/cc | 22.07 |
| 37 | 0.1% KYMENE 557 0.20 g/cc | 25.01 |
| 38 | 0.1% KYMENE 557 0.25 g/cc | 28.2 |
| 39 | 0.1% KYMENE 557 0.30 g/cc | 29.66 |

With reference to Table 8, it can be observed that changes in the density do not significantly change the amount of stabilized material within the absorbent structure. The amount of the stabilized layer largely depends on the chemical and physical properties of the wet-strength agent, and the amount of the wet-strength agent that is distributed into the absorbent structure.

EXAMPLE 9

A Vertical Wicking test was conducted on each sample of this Example, and the properties of the absorbent samples are summarized in the following Table 9.

TABLE 9

Liquid Wicking, Distribution Results

| Sample | Liquid add-on (gsm) | KYMENE % in spray liquid | Vertical Wicking flux g/min/gsm/inch (2.54 cm) |
|---|---|---|---|
| control | 0 | 0 | 0.000833 |
| 10-2kym | 10 | 2 | 0.002452 |
| 20-2kym | 20 | 2 | 0.002843 |
| 80-2kym | 80 | 2 | 0.002214 |
| 160-2kym | 160 | 2 | 0.001968 |
| 400-2kym | 400 | 2 | 0.001730 |

With reference to Table 9, it can be observed that absorbent structures stabilized with a wet-strength agent in a layered distribution can provides increased levels of vertical wicking performance.

EXAMPLES 10 and 11

For composites containing 25% and 40% of SAM, it has been observed that the amount of liquid wicked above a vertical height of 10 cm can be increased when the absorbent structure is stabilized with a layered distribution of an operative wet-strength agent, such as a KYMENE wet-strength agent.

Intermittent Vertical Wicking
(Percentage of liquid wicked above a height of 10 cm)

| | 1st % | 2nd % | 3rd % |
|---|---|---|---|
| 25% SAM | | | |
| Control | 0.95 | 7.82 | 21.92 |
| KYMENE Stabilized | 2.11 | 10.84 | 27.55 |

-continued

Intermittent Vertical Wicking
(Percentage of liquid wicked above a height of 10 cm)

| | 1st % | 2nd % | 3rd % |
|---|---|---|---|
| 40% SAM | | | |
| Control | 0.00 | 3.31 | 14.76 |
| KYMENE Stabilized | 0.23 | 6.14 | 19.85 |

EXAMPLE 12

The absorbent body of this example was composed of two, 200 gsm layers of CR1654 fluff with 20 gsm of solution add-on between the two layers of fluff at a 2% concentration of wet-strength agent in the solution. A sample of the absorbent body was prepared and analyzed in accordance with the procedures described in the Slope-Value Test.

Figure 9B:
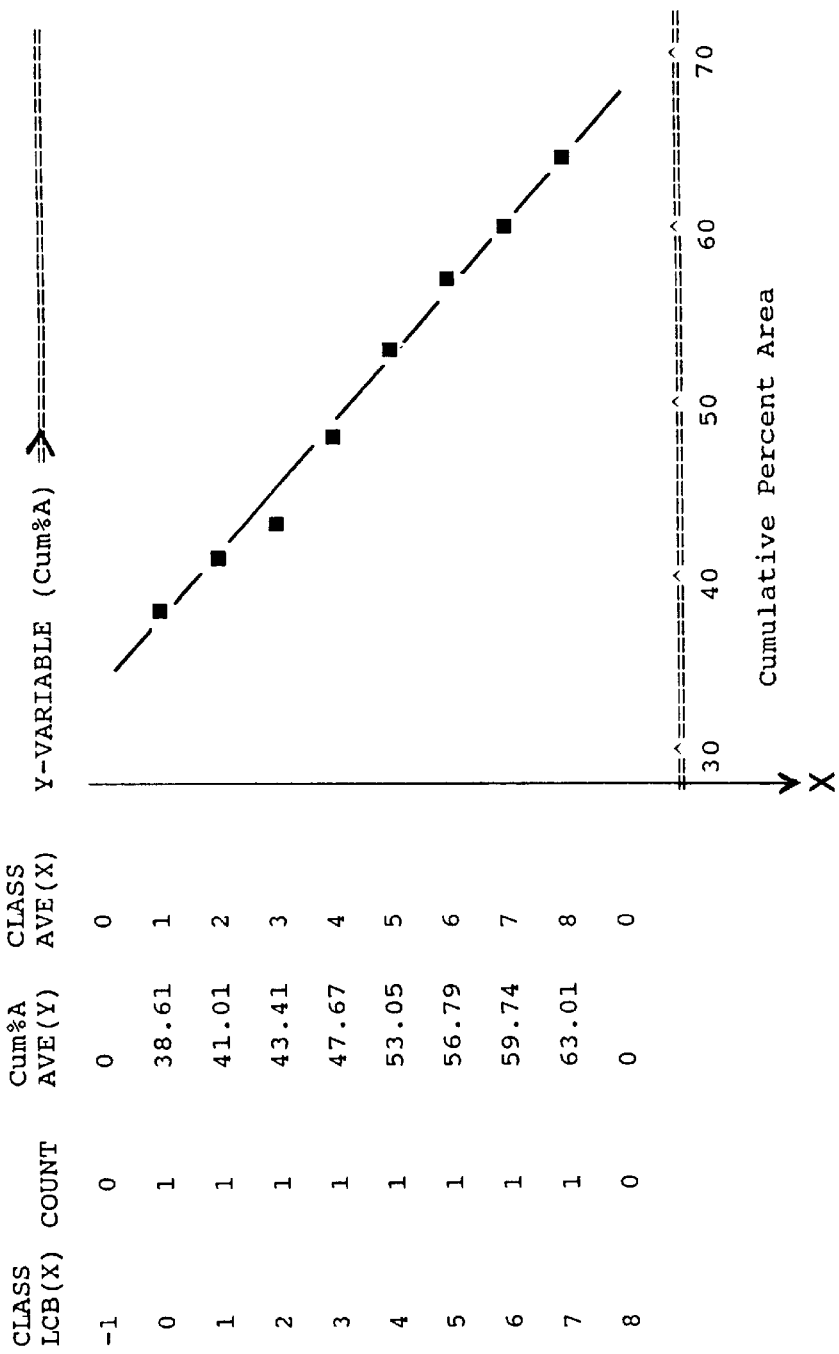
FIG. 9B shows a representative, graphic plot of the cumulative % A (y-axis) versus the class-difference (x-axis) generated by employing the data stream which begins at the "entry" field and ends at the "exit" field of a histogram of the type shown in FIG. 9A.
Figure 9C:
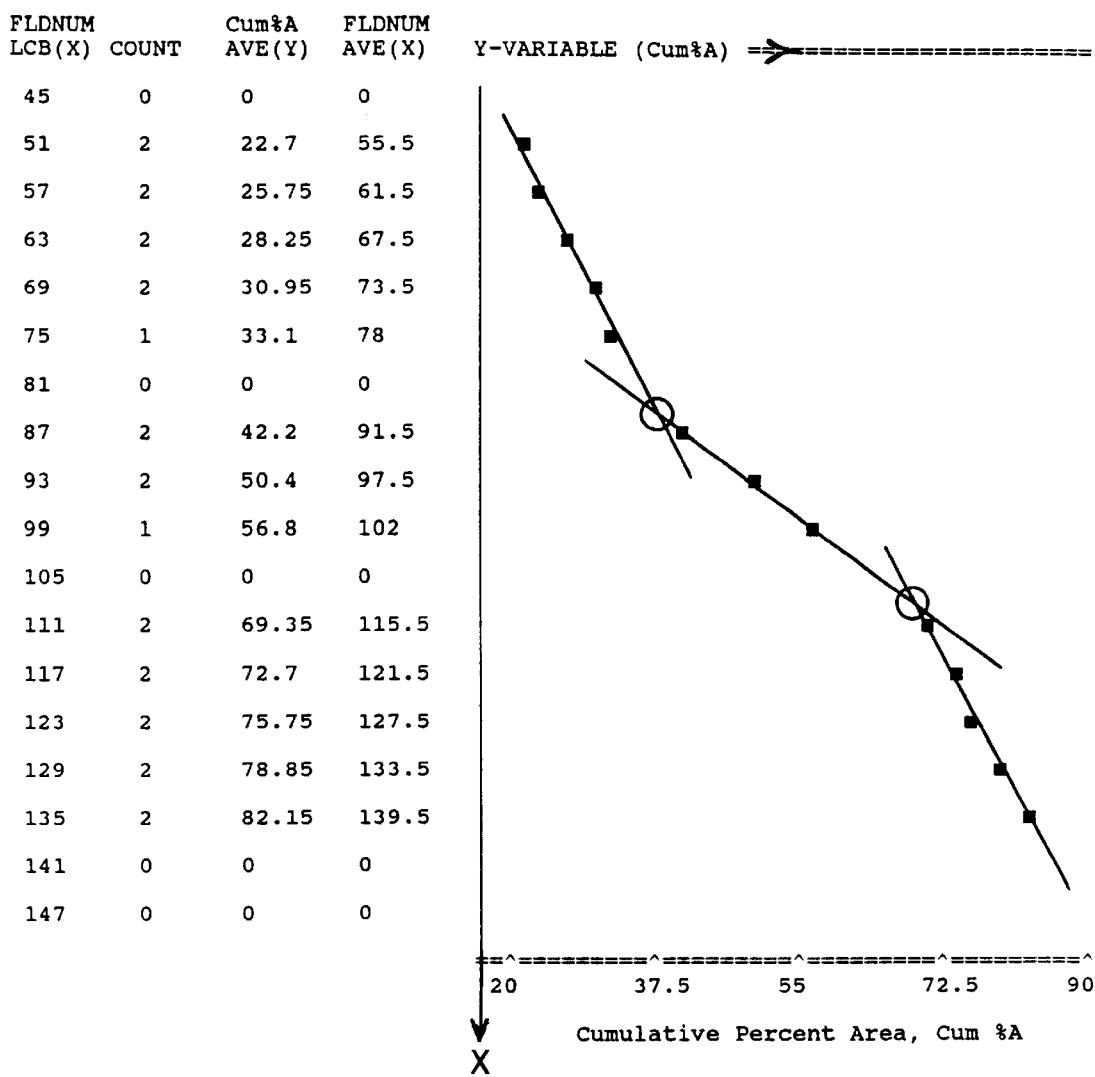
FIG. 9C representatively shows three lines that can be plotted by employing the data from the corresponding three regions of a histogram of the type shown in FIG. 9A to help determine the "entry" and "exit" fields of the histogram.

Three, thin-section specimens were sliced from the prepared sample. A schematic of an enlarged view of one of the thin-sectional specimens is representatively shown in FIG. 4, and a representative photomicrograph of one of the thin-sectional specimens is shown in FIG. 9. Two scans were conducted on each specimen, and each scan was located proximate one of the two opposed ends of the specimen. A histogram of the observed cumulative % A generated from a representative specimen of this Example is shown in FIG. 9A, and a representative, graphic plot of the cumulative % A (y-axis) versus the class-difference (x-axis) is shown in FIG. 9B. The sample of this example had a slope-value of 3.8.

EXAMPLE 13

The absorbent body of this example was composed of two, 200 gsm layers of CR1654 fluff with 8 layers of tissue between the fluff layers. A sample of the absorbent body was prepared and analyzed in accordance with the procedures described in the Slope-Value Test.

Figure 5:
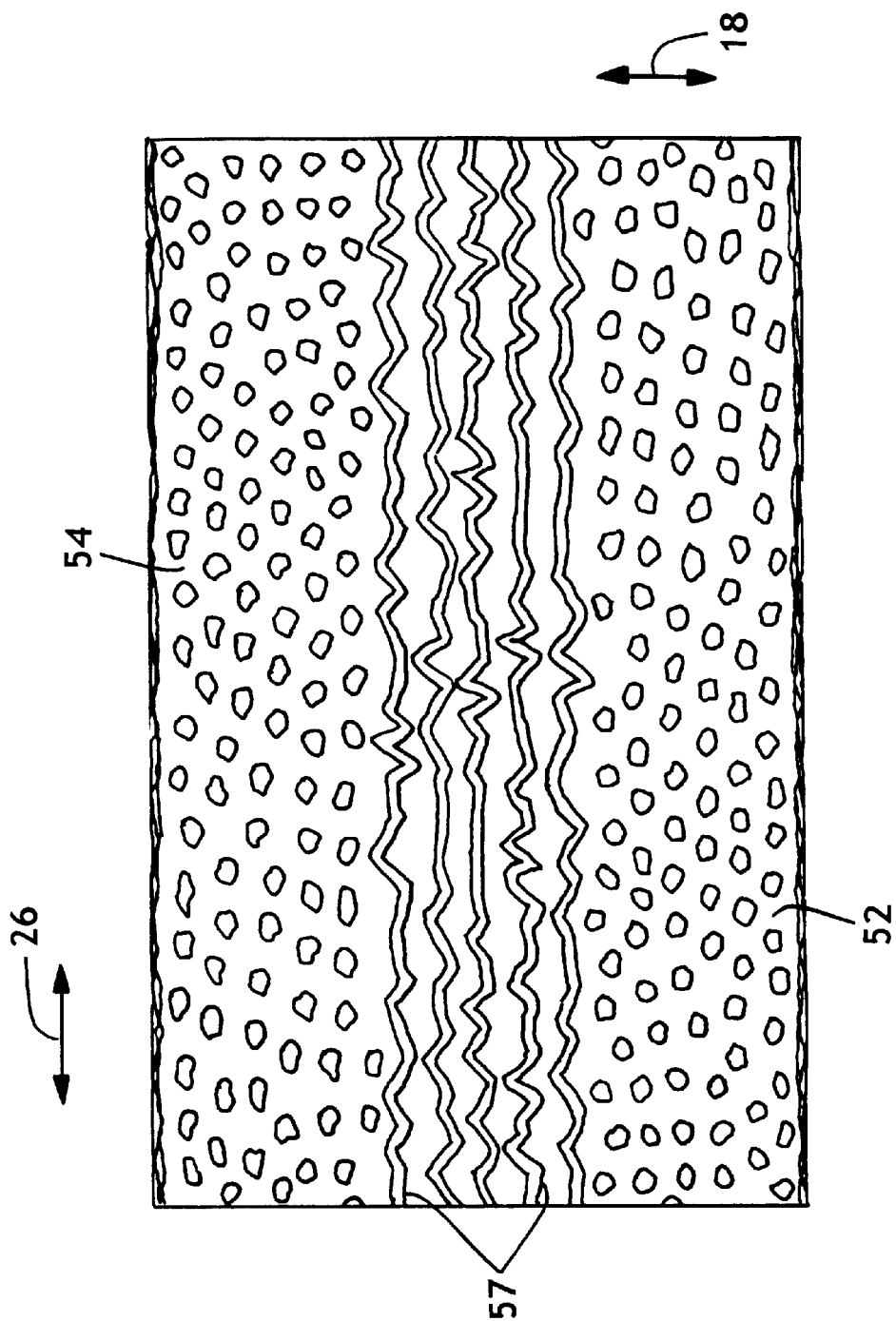
FIG. 5 representatively shows a schematic, enlarged, cross-sectional view of an absorbent body which includes a plurality of intermediate layers of tissue sandwiched between sheets of fibrous material.
Figure 10:
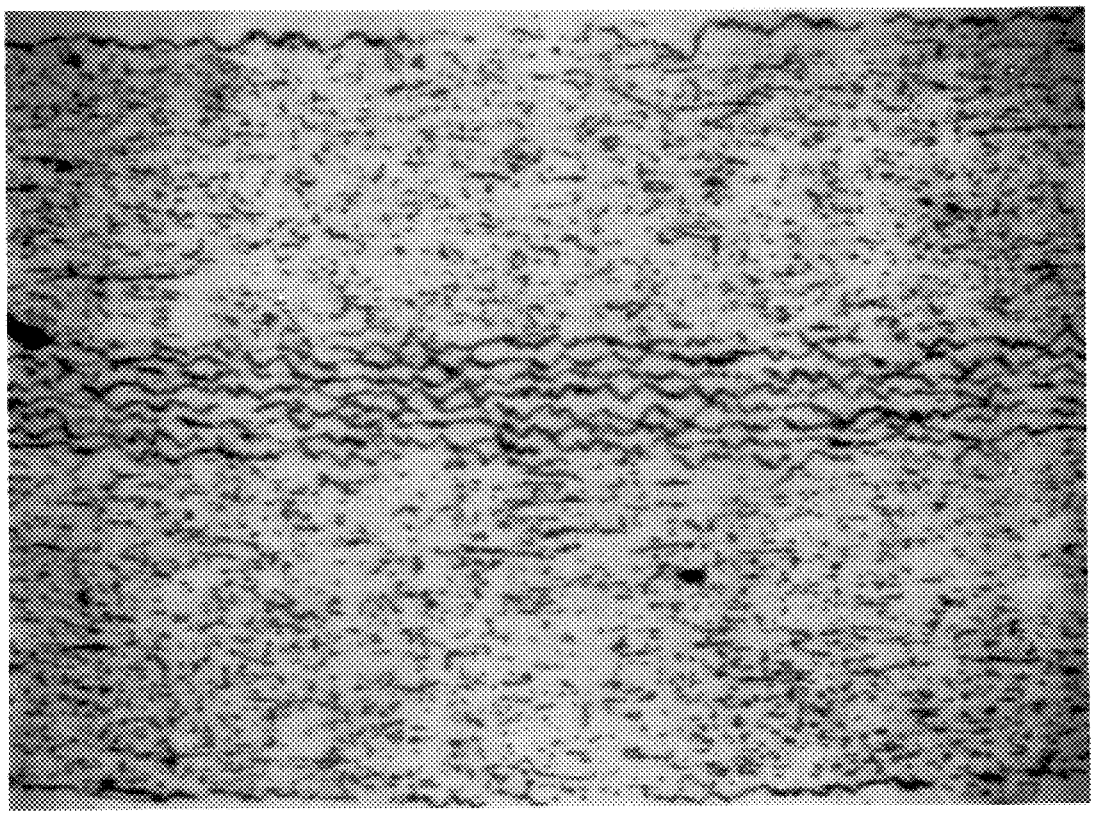
FIG. 10 representatively shows a photomicrograph of a thin-sectional specimen from a sample of an absorbent body which includes a plurality of intermediate tissue layers sandwiched between sheets of fibrous material.
Figure 10B:
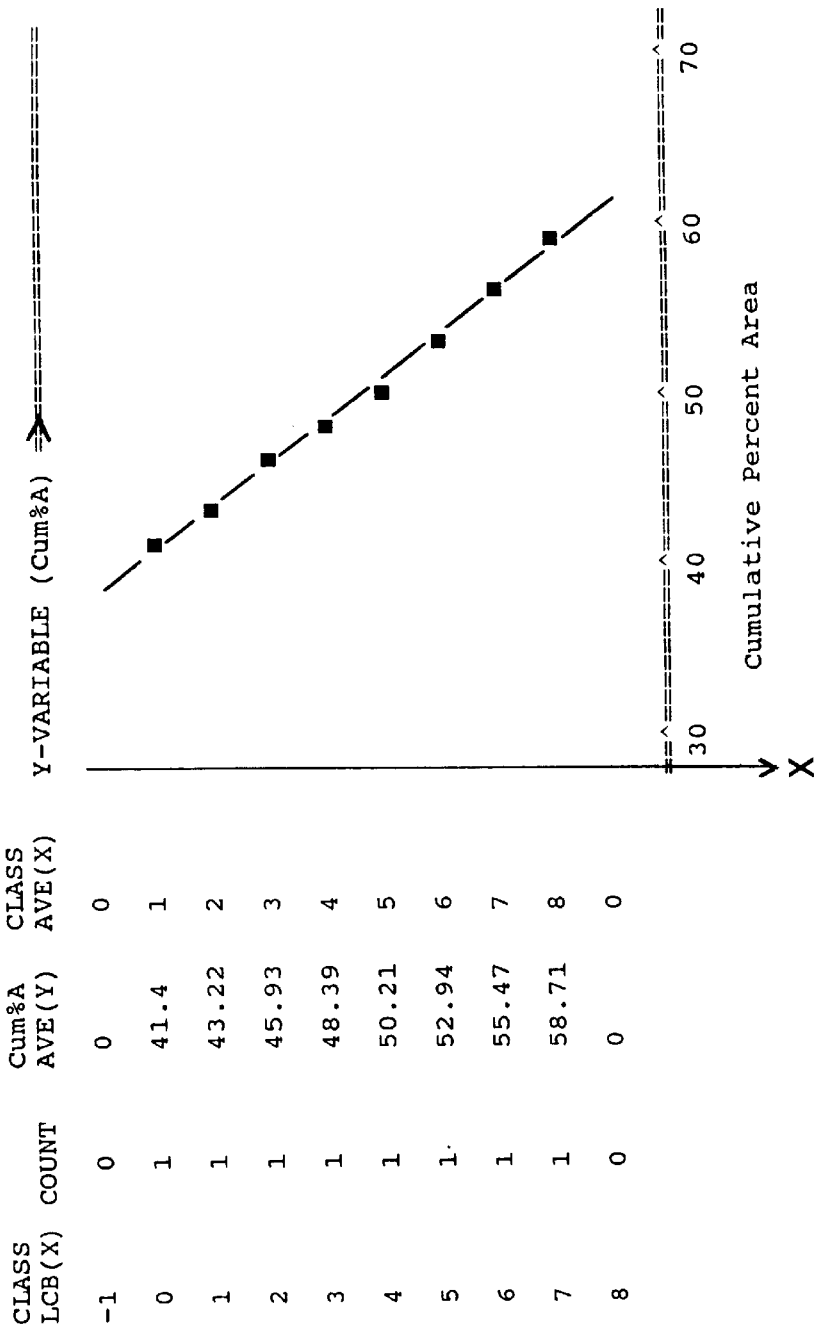
FIG. 10B shows a representative, graphic plot of the cumulative % A (y-axis) versus the class-difference (x-axis) generated by employing the data stream which begins at the "entry" field and ends at the "exit" field of a histogram of the type shown in FIG. 10A.

Three, thin-section specimens were sliced from the prepared sample. FIG. 5 representatively shows a schematic of an enlarged view of a thin-sectional specimen having multiple tissue layers 57, and FIG. 10 representatively shows a photomicrograph of one of the thin-sectional specimens taken from the sample employed in this Example. Two scans were conducted on each specimen, and each scan was located proximate one of the opposite ends of the specimen. A histogram of the observed cumulative % A generated from a representative specimen of this Example is shown in FIG. 10A, and a representative, graphic plot of the cumulative % A (y-axis) as a function of the class-difference (x-axis) is shown in FIG. 10B. The sample of this example had a slope-value of 2.4.

EXAMPLE 14

The absorbent body of this example was composed of two, 200 gsm layers of CR1654 fluff with one layer of tissue between the fluff layers. A sample of the absorbent body was prepared and analyzed in accordance with the procedures described in the Slope-Value Test.

Figure 11:
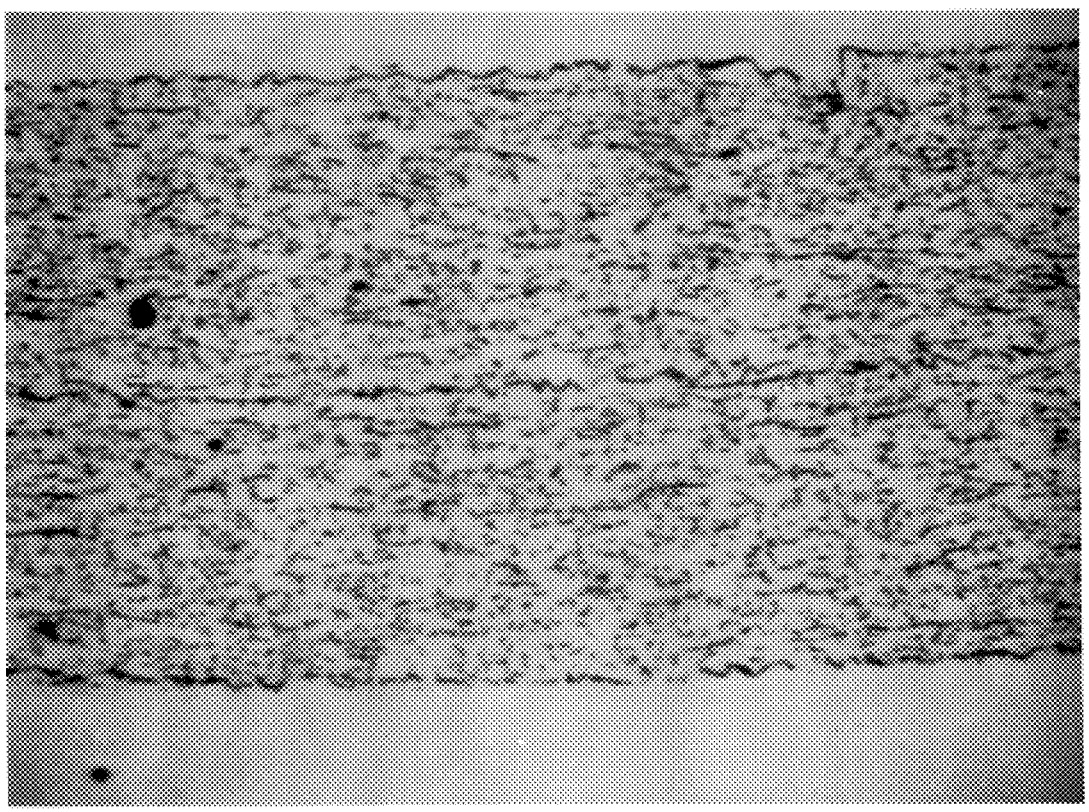
FIG. 11 representatively shows a photomicrograph of a thin-sectional specimen from a sample of an absorbent body having a single, intermediate layer of tissue.
Figure 11B:
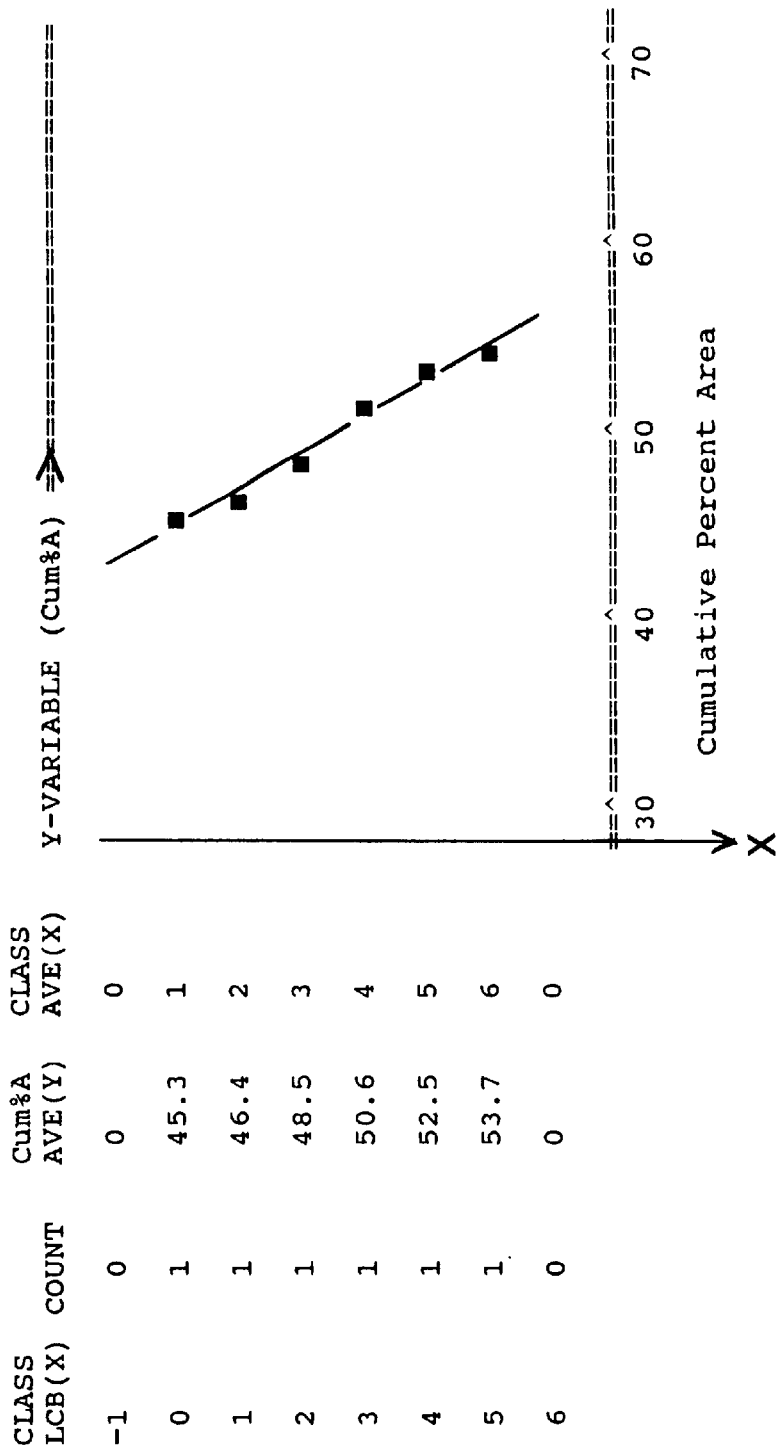
FIG. 11B shows a representative, graphic plot of the cumulative % A (y-axis) versus the class-difference (x-axis) generated by employing the data stream which begins at the "entry" field and ends at the "exit" field of a histogram of the type shown in FIG. 11A.

Three, thin-section specimens were sliced from the prepared sample. Two scans were conducted on each specimen, and each scan was located proximate one of the two opposed ends of the specimen. A photomicrograph of one of the thin-sectional specimens of this Example is representatively shown in FIG. 11. A histogram of the observed cumulative % A generated from a representative specimen is shown in FIG. 11A, and a representative, graphic plot of the cumulative % A versus the class-difference is shown in FIG. 11B. The sample of this example had a slope-value of 1.9.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article, comprising:
   a backsheet layer;
   a liquid permeable topsheet layer;
   an absorbent body sandwiched between said backsheet layer and said topsheet layer, said absorbent body including
   a first fibrous stratum,
   a second fibrous stratum,
   said first and second fibrous strata being composed of a substantially similar material, and at least a third fibrous stratum which is located between and integrally formed with said first
   and second fibrous strata, said third fibrous stratum including, a third quantity of absorbent fibers; and
   an operative quantity of a substantially hydrophilic, wet-strength agent which is distributed in said third fibrous stratum to render said third fibrous stratum substantially non-dispersible in an aqueous liquid.

2. An article as recited in claim 1, wherein said first and second fibrous strata are substantially free of said wet-strength agent.

3. An article as recited in claim 2, wherein said first and second fibrous strata are substantially dispersible in the aqueous liquid.

4. An article as recited in claim 1, wherein at least about 5 wt % of said absorbent body is substantially dispersible in the aqueous liquid.

5. An article as recited in claim 4, wherein said absorbent body provides a remainder basis weight which is substantially non-dispersible in the aqueous liquid, and said remainder basis weight is at least about 30 g/m².

6. An article as recited in claim 1, wherein said absorbent body has a liquid distribution value of at least about 0.001 g/(min*gsm*inch).

7. An article as recited in claim 1, wherein said absorbent body has a composite wet-strength of at least about 0.1 gm per g/m² per inch.

8. An article as recited in claim 1, wherein said wet-strength agent has been distributed to provide a dry add-on amount which is not more than about 1 wt % of said absorbent body.

9. An article as recited in claim 1, wherein said third fibrous stratum has been airlaid.

10. An article as recited in claim 9, wherein said first fibrous stratum has been airlaid.

11. An article as recited in claim 10, wherein said second fibrous stratum has been airlaid.

12. An article as recited in claim 1, wherein said third fibrous stratum is a non-tissue portion.

13. An article as recited in claim 1, wherein said absorbent body provides a slope-value which is at least about 2.6.

14. An article as recited in claim 13, wherein said absorbent body provides a slope-value which is not more than about 5.

15. An article as recited in claim 1, wherein said wet-strength agent includes a polyamide-polyamine-epichlorohydrin material.

16. An article as recited in claim 1, wherein said wet-strength agent has been distributed onto fibers of said third fibrous stratum during an airlaying of said third fibrous stratum.

17. An article as recited in claim 1, wherein said wet-strength agent has been distributed in a liquid form onto fibers of said third fibrous stratum.

18. An article as recited in claim 17, wherein said wet-strength agent has been distributed in a liquid solution form onto fibers of said third fibrous stratum.

19. An article as recited in claim 17, wherein said wet-strength agent has been distributed in an aqueous liquid form onto fibers of said third fibrous stratum.

20. An article as recited in claim 19, wherein said wet-strength agent has been sprayed onto fibers of said third fibrous stratum during an airlaying of said third fibrous stratum.

21. An article as recited in claim 1, wherein said absorbent body includes a quantity of superabsorbent material distributed therein.

22. An article as recited in claim 1, wherein said absorbent body has a composite density of at least about 0.05 g/cm³.

23. An article as recited in claim 1, wherein said absorbent body has a composite density of not more than about 0.4 g/cm³.

24. An article as recited in claim 1, wherein said third fibrous stratum and said second fibrous stratum have an irregular, diffuse interface therebetween.

25. An article as recited in claim 24, wherein said third fibrous stratum and said second fibrous stratum have an irregular, diffuse interface therebetween.

26. An article as recited in claim 1, wherein said article further comprises a surge management portion located adjacent said absorbent body.

27. An article as recited in claim 26, wherein said surge management portion is positioned between said absorbent body and said topsheet layer.

* * * * *